United States Patent
Palasis et al.

(10) Patent No.: US 7,491,234 B2
(45) Date of Patent: Feb. 17, 2009

(54) MEDICAL DEVICES FOR DELIVERY OF THERAPEUTIC AGENTS

(75) Inventors: Maria Palasis, Wellesley, MA (US); Wendy Naimark, Cambridge, MA (US); Robert E. Richard, Wrentham, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 640 days.

(21) Appl. No.: 10/308,587

(22) Filed: Dec. 3, 2002

(65) Prior Publication Data

US 2004/0106987 A1    Jun. 3, 2004

(51) Int. Cl.
A61F 2/06 (2006.01)
(52) U.S. Cl. ..................... 623/1.42; 424/423
(58) Field of Classification Search ................. 606/194; 623/1.15, 1.42; 424/423
See application file for complete search history.

(56) References Cited

U.S. PATENT DOCUMENTS

| | | | |
|---|---|---|---|
| 4,946,899 A | 8/1990 | Kennedy et al. | |
| 5,258,020 A | 11/1993 | Froiox | |
| 5,304,121 A | 4/1994 | Sahatjian | |
| 5,569,463 A | 10/1996 | Helmus et al. | |
| 5,578,075 A | 11/1996 | Dayton | 623/1 |
| 5,616,608 A | 4/1997 | Kinsella et al. | |
| 5,716,981 A | 2/1998 | Hunter et al. | |
| 5,733,925 A | 3/1998 | Kunz et al. | |
| 5,741,331 A | 4/1998 | Pinchuk | |
| 5,879,697 A | 3/1999 | Ding et al. | |
| 5,954,706 A | 9/1999 | Sahatjian | |
| 6,096,070 A | 8/2000 | Ragheb et al. | |
| 6,099,652 A | 8/2000 | Ding et al. | |
| 6,120,491 A | 9/2000 | Kohn et al. | |
| 6,143,037 A | 11/2000 | Goldstein et al. | |
| 6,153,252 A | 11/2000 | Hossainy et al. | |
| 6,187,370 B1* | 2/2001 | Dinh et al. | 427/2.24 |
| 6,245,103 B1 | 6/2001 | Stinson | |
| 6,280,411 B1 | 8/2001 | Lennox | |
| 6,335,029 B1 | 1/2002 | Kamath et al. | |
| 2002/0107330 A1* | 8/2002 | Pinchuk et al. | 525/242 |
| 2002/0127265 A1* | 9/2002 | Bowman et al. | 424/426 |
| 2006/0193890 A1* | 8/2006 | Owens et al. | 424/423 |

FOREIGN PATENT DOCUMENTS

| | | |
|---|---|---|
| DE | 19713214 A1 | 12/1998 |
| EP | 0841040 A1 | 5/1998 |
| WO | WO 98/56312 | 12/1998 |
| WO | WO 99/00071 | 1/1999 |

* cited by examiner

Primary Examiner—Kevin T Truong
Assistant Examiner—Victor X Nguyen
(74) Attorney, Agent, or Firm—Mayer & Williams PC; David B. Bonham, Esq.; Keum J. Park, Esq.

(57) ABSTRACT

The present invention is generally directed to medical devices, and more specifically to medical devices that are at least partially insertable or implantable into the body of a patient. The medical devices generally comprise (a) a therapeutic agent, more typically, a high-molecular-weight therapeutic agent, and (b) at least one polymeric layer, which typically acts to control the release of the therapeutic agent from the medical device. Also disclosed herein are methods of making such medical devices.

25 Claims, 10 Drawing Sheets

MEDICAL DEVICES FOR DELIVERY OF THERAPEUTIC AGENTS

FIELD OF THE INVENTION

The present invention relates to implantable or insertable medical devices, such as intraluminal stents, that release therapeutic agents. The medical devices of the present invention are particularly appropriate for the release of high molecular weight therapeutic agents, such as DNA.

BACKGROUND OF THE INVENTION

Percutaneous transluminal coronary angioplasty ("PTCA" or "angioplasty") procedures have been performed for many years as an adjunct to correcting vascular disease in patients. Angioplasty procedures involve the insertion, through the vascular system, of a catheter having a balloon that is placed across a lesion or blockage in a coronary artery. The balloon is then inflated to compress the lesion or blockage against the arterial walls, thereby opening the artery for increased blood flow.

In some cases, however, the goal of the angioplasty procedure is defeated at least in part by a complete or partial reclosure of the artery at or near the compressed lesion or blockage. Two mechanisms are believed to be principally responsible for reclosure of the artery. The first mechanism is recoil, which is a mechanical process involving the elastic rebound of the compressed lesion or blockage. The second mechanism is restenosis, which is believed to be caused by proliferation of the smooth muscle cells present in the artery walls near the lesion or blockage. Restenosis can occur over a period of several weeks or months after the PTCA procedure.

Many different methods have been employed to limit the effect of restenosis, including radiation treatments and various drug therapies, delivered locally and systemically, to slow proliferation of the smooth muscle cells. Recoil of the arterial walls can be prevented by using stents, which can be temporarily or permanently deployed within the artery to mechanically maintain patency of the artery. Stents are very effective at carrying out this task, but they may also irritate the contacting arterial walls, which may in turn encourage additional restenosis.

Gene therapy has been used for diverse medical purposes, including slowing proliferation of smooth muscle cells. Genes are usually delivered into a patient's cells through a vector, such as a retroviral vector, whose DNA is genetically engineered to include a desired DNA sequence. Alternatively, nonviral gene transfer methods can be used, such as plasmid DNA vectors, along with polymeric carriers, DNA condensing agents, lipofection and receptor mediated delivery vectors.

In connection with angioplasty, incorporation of appropriate DNA molecules into the coronary artery walls near the treatment site can be beneficial to inhibit restenosis. A polymer-coated stent can be used as the delivery vehicle for the DNA, in addition to maintaining patency of the artery following PTCA.

However, effective delivery of high-molecular-weight therapeutic agents, such as DNA and any associated vector, can entail large amounts of therapeutic agent and long delivery times. Large amounts of polymeric material provided as a coating on the stent may, therefore, be required to adequately incorporate the therapeutic agent and ensure controlled and extended release of the therapeutic agent over a required period of time. Consequently, the polymeric coating may become relatively thick, increasing the susceptibility, during expansion of the stent, to cracking of the coating. Such cracking can reduce the effectiveness of the coating to deliver the therapeutic agent therefrom, among other consequences. Moreover, because some medical devices such as stents have limited surface areas for disposition of a polymer coating, it would be desirable to provide a coating that actually enhances the uptake of the therapeutic agent by the tissue of interest.

The manufacture of medical devices with high-molecular-weight therapeutic agents in polymer matrices can also present processing difficulties. For example, relatively high shear stresses are commonly encountered while processing a mixture of a polymeric material and a therapeutic agent. In the case of certain high-molecular-weight therapeutic agents such as polynucleotides (e.g., plasmids), for example, these shear stresses can, in turn, disrupt the conformational and/or structural integrity of the therapeutic agent.

Moreover, certain biostable polymers that are highly biocompatible (e.g., polystyrene-polyisobutylene copolymers) may in some cases provide insufficient mass transport therethrough of high-molecular-weight therapeutic agents after deployment, limiting their utility in medical devices that deliver such agents.

Accordingly, there is a need for coatings for stents and other medical devices that release high-molecular-weight therapeutic agents in a controlled fashion over a period of time and do not suffer from the foregoing and other disadvantages. The coatings should, therefore, contain a therapeutically effective amount of high-molecular-weight therapeutic agent and provide adequate control of the release of that therapeutic agent. In addition, in the case of expandable medical devices such as stents and balloons, the coatings should resist cracking that may occur during expansion of the medical device. Moreover, the conformational and structural integrity of high-molecular-weight therapeutic agents such as DNA should be preserved to the greatest extent possible during manufacture of the medical device.

SUMMARY OF THE INVENTION

These and other needs are met by the present invention.

According to one aspect of the present invention, a medical device is provided, at least a portion of which is insertable or implantable into the body of a patient. The medical device comprises: (a) a plasmid DNA layer, which comprises plasmid DNA; and (b) a polymeric covering layer disposed over the plasmid DNA layer.

Examples of implantable or insertable medical devices include catheters, balloons, filters, coils, clips, slings, and intraluminal stents, for instance, vascular stents.

The plasmid DNA layer may be applied in a number of ways, for example, by dipping at least a portion of the medical device into a solution comprising the plasmid DNA.

The polymeric covering layer can be, for example, a biostable polymeric covering layer or a biodisintegrable polymeric covering layer.

Examples of biostable polymeric covering layers include those that comprise one or more of the following: polyolefin polymers and copolymers; ethylenic copolymers; polyurethane polymers and copolymers; metallocene catalyzed polyethylene polymers and copolymers; ionomers; polyester-ether polymers and copolymers; polyamide-ether polymers and copolymers; and silicone polymers and copolymers.

The biostable polymeric covering layer can comprise, for example, a block copolymer comprising at least two polymeric blocks A and B, wherein A is a polyolefin block and B is a vinyl aromatic block. For example, A can be a polyolefin block of the general formula —(CRR'—CH$_2$)$_n$—, where R and R' are linear or branched aliphatic groups or cyclic aliphatic groups and B can be is a vinyl aromatic polymer block. As another example, A can be a polyolefin block that comprises one or more monomers selected from ethylene, butylene and isobutylene, and B can be a vinyl aromatic polymer block that comprises one or more monomers selected from styrene and α-methylstyrene.

Examples of biodisintegrable polymeric covering layers include those that comprise one or more of the following: lactic acid polymers and copolymers, glycolic acid polymers and copolymers, trimethylene carbonate polymers and copolymers, caprolactone polymers and copolymers, hyaluronic acid polymers and copolymers, hydroxybutyrate polymers and copolymers, and tyrosine-based polymers and copolymers.

The biodisintegrable polymeric covering layer can comprise, for example, (a) hyaluronic acid polymers, (b) copolymers of lactic acid and glycolic acid, and/or (c) tyrosine-derived polycarbonates.

According to another aspect of the present invention, a medical device is provided, at least a portion of which is insertable or implantable into the body of a patient. The medical device comprises (a) a therapeutic agent containing layer, which comprises a high-molecular-weight therapeutic agent; and (b) a polymeric covering layer disposed over the high-molecular-weight-therapeutic-agent layer. The polymeric covering layer comprises one or more polymers selected from (i) a block copolymer comprising at least two polymeric blocks A and B, wherein A is a polyolefin block and wherein B is a vinyl aromatic block, (ii) a polymer or copolymer of lactic acid, (iii) a polymer or copolymer of glycolic acid, and (iv) a tyrosine-based polymer or copolymer.

The therapeutic agent containing layer may be applied in a number of ways, for example, by dipping at least a portion of the medical device into a solution comprising the high-molecular-weight therapeutic agent.

Examples of high-molecular-weight therapeutic agents include: (a) polysaccharide therapeutic agents having a molecular weight greater than 1,000; (b) polypeptide therapeutic agents having a molecular weight greater than 10,000; and (c) polynucleotides having a molecular weight greater than 2,000, for instance, plasmid DNA.

According to another aspect of the present invention, a medical device is provided, at least a portion of which is insertable or implantable into the body of a patient. The medical device comprises (a) polymeric layer comprising a removable component as well as (i) a block copolymer comprising at least two polymeric blocks A and B, wherein A is a polyolefin block and B is a vinyl aromatic block and/or (ii) a tyrosine-based polymer or copolymer; and (b) a high-molecular-weight therapeutic agent disposed below or within the polymeric layer.

The removable component can be, for example, a leachable material, such as polyethylene glycols, polyalkylene oxides (e.g., polyethylene oxide and copolymers of polyethylene oxide and polypropylene oxide), polyhydroxyethylmethacrylates, polyvinylpyrrolidones, polyacrylamide and its copolymers, liposomes, proteins, peptides, salts, sugars, polysaccharides, polylactides, cationic lipids, detergents, polygalactides, polyanhydrides, polyorthoesters and their copolymers, and soluble cellulosics.

According to another aspect of the present invention, a medical device is provided, at least a portion of which is insertable or implantable into the body of a patient. The medical device comprises (a) a polymeric layer comprising a polymer and a plasticizer; and (b) a high-molecular-weight polynucleotide therapeutic agent (e.g., plasmid DNA) disposed below or within the polymeric layer.

The plasticizer can be, for example, glycerol, triacetyl glycerin, ethylene glycol, triethylene glycol, polyethylene glycol, propylene glycol, polyalkylene oxides (e.g., polyethylene oxide and copolymers of polyethylene oxide and polypropylene oxide), citric acid esters, sebacic acid esters, phthalic acid esters, and silicone fluid.

According to another aspect of the present invention, a medical device is provided, at least a portion of which is insertable or implantable into the body of a patient. The medical device comprises a multi-layer coating that covers at least a portion of the medical device. The multi-layer coating further comprises (a) one or more therapeutic agent containing layers comprising a therapeutic agent and (b) one or more polymeric layers comprising a polymer, wherein the one or more polymeric layers have a composition gradient in a direction normal to the surface of the coating.

The therapeutic agent can be, for example, a high-molecular-weight therapeutic agent.

The one or more therapeutic agent containing layers can be disposed, for example, beneath the one or more polymeric layers. In an alternative embodiment, a plurality of therapeutic agent containing layers are disposed in an alternating configuration with a plurality of polymer layers.

In some embodiments, the composition gradient is provided within a single polymeric layer. In others, the composition gradient is provided within a plurality of polymeric layers (e.g., 2, 3, 4, 5 or more polymeric layers).

The composition gradient can comprise, for example, (a) a gradient in porosity, (b) a gradient in polymer composition, for example, a gradient in the relative proportions of two or more monomer species within a copolymer or a gradient in the relative proportions of two or more polymers within a polymer blend (for example, the relative proportions of a hydrophobic polymer, such as styrene-isobutylene copolymer, and a hydrophilic polymer, such as a styrene-ethylene oxide copolymer), (c) a gradient in the composition of a leachable species, (d) a gradient in the composition of an acidic species, (e) a gradient in the composition of a basic species and/or (f) a gradient in the composition of an ionic species.

One advantage of the present invention is that polymer coated medical devices such as stents, containing therapeutic agents, including high-molecular-weight therapeutic agents such as DNA, can be provided in which the rate of release of the therapeutic agents is adequately regulated so as to provide a therapeutically effective amount of such agent over a desired period of time.

Another advantage of the present invention is that polymer coated medical devices, such as stents, containing therapeutic agents, including high-molecular-weight therapeutic agents such as DNA, can be provided in which the polymer resists cracking upon expansion of the medical device.

Another advantage of the present invention is that medical devices such as stents, containing therapeutic agents, including high-molecular-weight therapeutic agents such as DNA, can be provided wherein the structural integrity of the therapeutic agent is not substantially disrupted during medical device manufacture.

Yet another advantage of the present invention is that medical devices such as stents, containing therapeutic agents, and particularly high-molecular-weight therapeutic agents such as DNA, can be provided in which the uptake of the therapeutic agent by the targeted tissue is enhanced.

These and other embodiments and advantages of the invention will become apparent from the following detailed description, and the accompanying drawings, which illustrate by way of example the features of the invention.

DETAILED DESCRIPTION OF THE INVENTION

The various embodiments of the present invention are directed to implantable or insertable medical devices in which a polymer coating layer is used to regulate local delivery of a therapeutic agent, and typically a high-molecular-weight therapeutic agent, as defined below.

Localized delivery of a therapeutic agent from an implantable or insertable medical device is advantageous, because higher local concentrations of the therapeutic agent and/or more regulated delivery thereof can be achieved than with systemic administration. Consequently, increased cellular uptake of the therapeutic agent and therapeutic efficacy can be achieved with localized delivery, as opposed to systemic delivery of the therapeutic agent.

For example, systemic administration of several doses of therapeutic agent typically results in peaks and troughs in the level of concentration received by the tissue. In some cases, the peaks may be higher than a maximum desired level, leading to undesirable side effects, for example, and the troughs may be lower than a minimum effective level for the therapeutic agent. On the other hand, local administration of the therapeutic agent, for example, via a coated stent, can provide a concentration level of delivered agent that remains within a therapeutically effective range for a longer period of time.

The present invention is applicable to implantable or insertable medical devices of any shape or configuration. Examples of medical devices appropriate for the practice of the present invention include intraluminal catheters (including vascular catheters such as balloon catheters), guide wires, balloons, filters (e.g., vena cava filters), stents, stent grafts, cerebral stents, cerebral aneurysm filler coils (including metal coils and GDC—Guglilmi detachable coils), clips, slings, vascular grafts, myocardial plugs, pacemaker leads and heart valves.

More specific examples of medical devices for the practice of the present invention include intraluminal stents such as endovascular, biliary, tracheal, gastrointestinal, urethral, ureteral, esophageal and coronary vascular stents. The intraluminal stents of the present invention may be, for example, balloon-expandable or self-expandable. Thus, although certain embodiments of the present invention will be described herein with reference to vascular stents, the present invention is applicable to other medical devices, including other types of stents.

In general, stents for use in connection with the present invention typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

Figure 1:
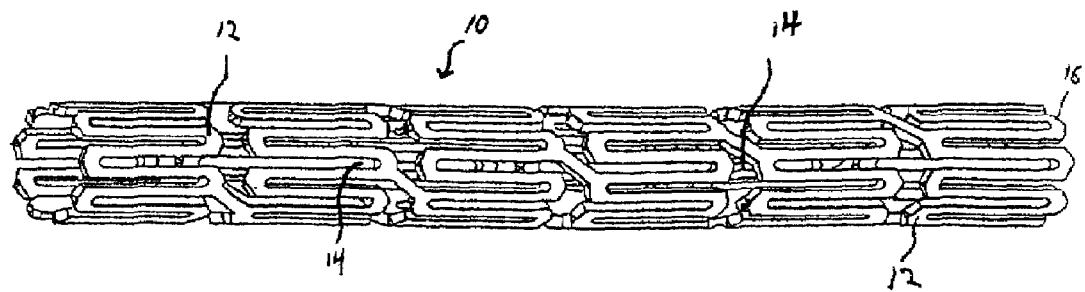
FIG. 1 is a schematic diagram of a stent with a polymer coating, according to an embodiment of the invention.
Figure 2:
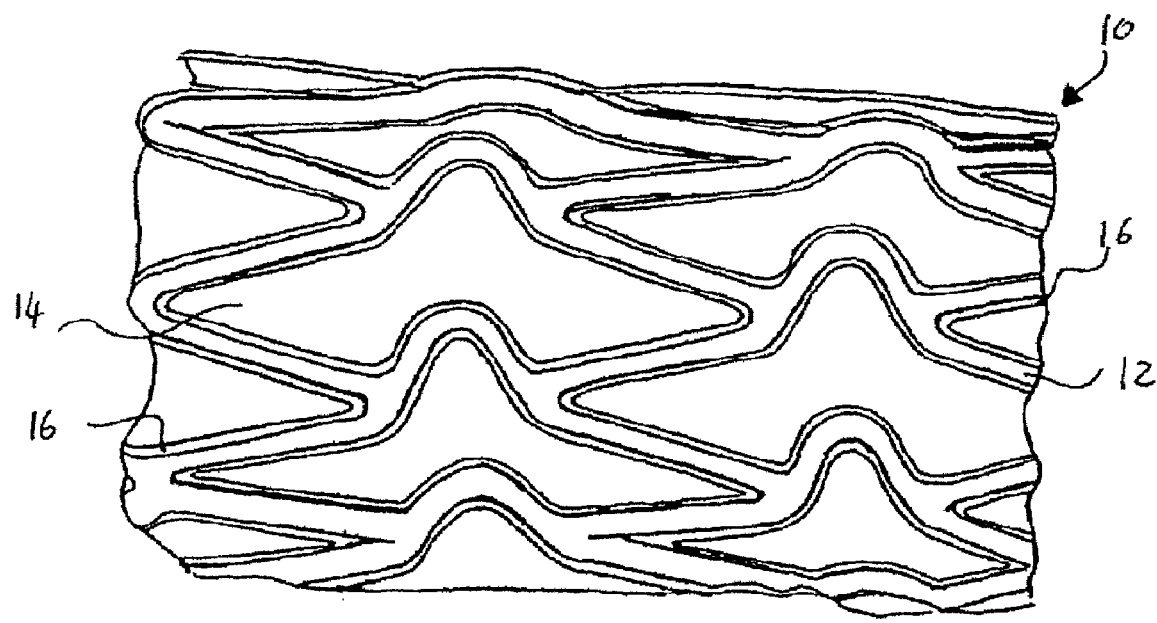
FIG. 2 is a schematic diagram of a stent with a polymer coating, according to an embodiment of the invention.
Figure 3:
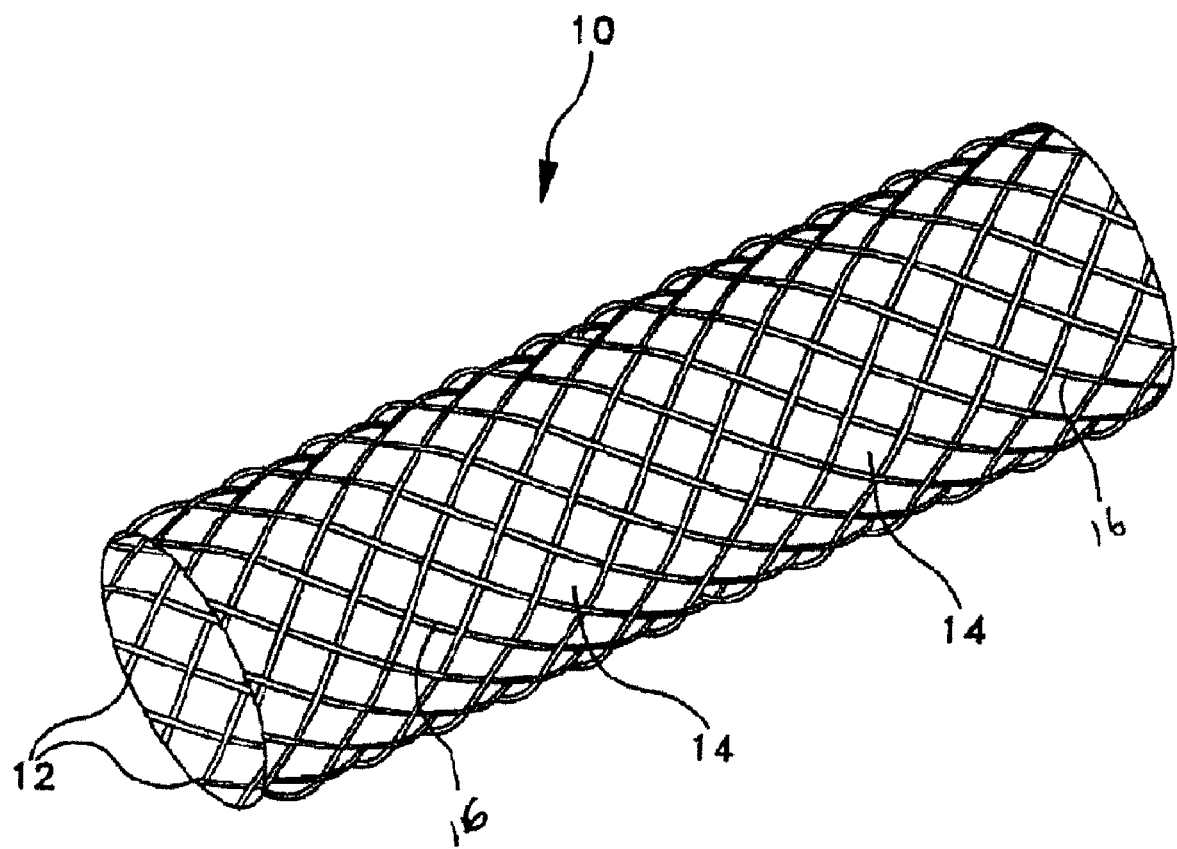
FIG. 3 is a schematic diagram of a stent with a polymer coating, according to an embodiment of the invention.

FIGS. 1 and 3 illustrate two embodiments of polymer coated endovascular stents 10 according to the present invention. FIG. 2 shows a detailed enlargement of a portion of a polymer-coated stent that is similar in design to that shown in FIG. 1. Each stent 10 can be, for example, a coronary stent sized to fit in the blood vessel of a patient, which is formed from a plurality of structural elements 12. The construction of each stent 10 permits the stent 10 to be introduced into the vascular system in a collapsed configuration, minimizing the diameter of the stent 10. Each stent 10 can then expand to an expanded position at the desired location within the blood vessel of the patient. The structural elements 12 of each stent 10 form a conventional frame, such as tubular shape, and permits the stent 10 to self-expand or to expand to the desired shape after an expansive force is applied, for example, by the expansion of a balloon within the stent.

A coating 16 is applied on the surface of each stent 10. According to the present invention, coating 16 can include either a biostable or biodisintegrable polymer as described more fully below, which contains, or is provided as a coating over, a therapeutic agent. The therapeutic agent is released in a controlled manner after introduction of the stent 10 into the body of the patient. As one specific example, in the case of high-molecular-weight therapeutic agent such as plasmid DNA, a typical coronary stent can have a uniform coating of approximately 1,000 micrograms in weight or more, which contains up to 100 micrograms of plasmid DNA or more.

The structural elements 12 of each stent 10 form windows 14 such that the stent 10 does not have a continuous outer shell. Windows 14 are generally present in most stent configurations, although the specific details of the shape of structural elements 12 and the construction of stent 10 can vary as can be seen, for example, from FIGS. 1-3. Each stent 10 can thus be coated with polymeric coating 16 such that windows 14 remain free of coating. Alternatively, each stent 10 can be covered by coating 16 such that a layer or web of coating (not shown) also covers the windows 14 between elements 12. For certain embodiments, it is beneficial that the windows 14 be left free of a covering. The unobstructed windows: (a) allow a freer exchange of nutrients between the inner walls of the vessel and the fluid flowing through the vessel, such as blood flowing in an artery and (b) do not block flow to vessel side-branches. In alternate embodiments, the material filling the windows is sufficiently porous to allow exchange of nutrients and oxygen.

Various embodiments of the invention can be implemented by dipping a medical device of interest into a solution (e.g., a solution containing a polymer and a high-molecular-weight therapeutic agent). In such embodiments, it may be desirable to employ a stent holder, such as those known in the art, which facilitates placing the stent in solution and subsequently removing and spinning the stent to remove excess solution.

Typical sites for placement of the medical devices of the present invention include the coronary and peripheral vasculature (collectively referred to herein as the vasculature), esophagus, trachea, colon, gastrointestinal tract, biliary tract, urinary tract, prostate, brain and surgical sites. Where the medical device is inserted into the vasculature, for example, the therapeutic agent is may be released to a blood vessel wall adjacent the device, and may also be released to downstream vascular tissue as well.

After the medical devices of the present invention are deployed at a suitable site, the therapeutic agent is released and delivered locally to tissue adjacent the medical device. Depending upon the application, various release profiles can be provided in accordance with the present invention including: (a) 50% release (i.e., 50% of the total release from the medical device that occurs over the prescribed course of implantation/insertion) occurring during a period of 15-60 minutes after implantation/insertion, (b) 50% release occurring over a period of 1-6 hours, (b) 50% release occurring over a period of 6-24 hours, (c) 50% release occurring over a period of 24-96 hours (4 days), (d) 50% release occurring over a period of 4-14 days, (e) 50% release occurring over a period of 2-8 weeks, (f) 50% release occurring over a period of 8-32 weeks.

Typical subjects (also referred to herein as "patients") are vertebrate subjects (i.e., members of the subphylum cordata), including, mammals such as cattle, sheep, pigs, goats, horses, dogs, cats and humans.

"Therapeutic agents", "pharmaceutically active agents", "pharmaceutically active materials", "drugs" and other related terms may be used interchangeably herein and include genetic therapeutic agents, non-genetic therapeutic agents, and cells.

Exemplary non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-mitotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents include anti-sense DNA and RNA, oligo decoys, as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently beneficial BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Cells include cells of human origin (autologous or allogeneic), including stem cells and platelets, or from an animal source (xenogeneic), which can be genetically engineered if desired to deliver proteins of interest.

Numerous therapeutic agents, not necessarily exclusive of those listed above, have been identified as candidates for vascular treatment regimens, for example, as agents targeting restenosis. Such agents are appropriate for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naffidrofuryl, as well as 5-HT uptake inhibitors such as fluoxetine, (c) cyclic nucleotide pathway agents including phosphodiesterase inhibitors such as cilostazole and dipyridamole, adenylate/guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (1) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, (cc) blood rheology modulators such as pentoxifylline, and (dd) endothelial-cell specific mitogens.

Further therapeutic agents appropriate for the practice of the present invention, again not necessarily exclusive of those listed above, are also disclosed in U.S. Pat. No. 5,733,925 assigned to NeoRx Corporation, the entire disclosure of which is incorporated by reference.

The present invention is especially useful in delivering high-molecular-weight therapeutic agents, which are defined herein to include therapeutic agents having a molecular weight greater than 500, typically greater than 1,000, more typically greater than 2,000, or agents which contain one or more components having such molecular weights. Examples are polysaccharide therapeutic agents having a molecular weight greater than 1,000; polypeptide therapeutic agents having a molecular weight greater than 10,000; polynucleotides, including antisense polynucleotides, having a molecular weight greater than 2,000, gene-encoding polynucleotides, including plasmids, having a molecular weight greater than 500,000; viral and non-viral particles having a diameter greater than about 50 nanometers, and cells.

A "polynucleotide" is a nucleic acid polymer. A polynucleotide can include both double- and single-stranded sequences, and can include naturally derived and synthetic DNA sequences. The term also includes sequences that include any of the known base analogs of DNA and RNA, and includes modifications, such as deletions, additions and substitutions (generally conservative in nature) to native sequences. In some embodiments of the invention, the polynucleotide can be, for example, an antisense polynucleotide. In others, polynucleotide can be, for example, of transfection unit length, which is typically on the order of about 1 kb or greater.

Typical polynucleotide therapeutic agents include the genetic therapeutic agents specifically listed above, and more generally include DNA encoding for various polypeptide and protein products including those previously listed. Some additional examples of polynucleotide therapeutic agents include DNA encoding for the following: cytokines such as colony stimulating factors (e.g., granulocyte-macrophage colony-stimulating factor), tumor necrosis factors (e.g., fas ligand) and interleukins (e.g., IL-10, an anti-inflammatory interleukin), as well as protease inhibitors, particularly serine protease inhibitors (e.g., SERP-1), tissue inhibiting metalloproteinases (e.g., TIMP-1, TIMP-2, TIMP-3, TIMP-4), monocyte chemoattractant proteins (e.g., MCP-1), protein kinase inhibitors including cyclin-dependent kinase inhibitors (e.g., p27, p21), endogenous and inducible nitric oxide synthase, CO-generating enzymes, such as hemoxygenases, which catalyze the oxidation of heme into the biologically active molecules iron biliverdin and CO (e.g., HOI-1), antiproliferative compounds, such as hKIS in a transdominant mutant peptide form, which are capable of interfering with the ability of endogenous hKIS to phosphorylate p27 thereby enhancing cell cycle arrest, as well as derivatives of the foregoing.

Vectors of interest for delivery of polynucleotide therapeutic agents include (a) viral vectors such as adenovirus, adenoassociated virus and lentivirus, and (b) non-viral vectors such as DNA plasmid, along with condensing agents, receptor mediated delivery vectors, polymeric carriers, lipids (including cationic lipids), and liposomes.

The term "polypeptide" refers to a polymer of amino acid residues. Both full-length proteins and fragments thereof are encompassed by the definition. The terms also include modifications, such as deletions, additions and substitutions (generally conservative in nature), to native sequence. Exemplary polypeptides include any of the polypeptides/proteins listed in the preceding paragraphs.

The term "polysaccharide" refers to a polymer of monosaccharide residues. Typical polysaccharides include any of the polysaccharides listed in the preceding paragraphs. Low and high molecular weight heparin and dextran, including derivatives of the same, for example, dextran sulfate salts and dextran-metal complexes such as dextran-iron complex, are some exemplary polysaccharides.

Hybrids of the above high-molecular-weight therapeutics (e.g., DNA/protein hybrids and polysaccharide/protein hybrids) are also within the scope of the present invention.

Some specific classes of high-molecular-weight therapeutic agents are anti-proliferative agents, anti-inflammatory agents, anti-thrombotic agents, lipid mediators, vasodilators, anti-spasm agents, remodeling agents, endothelial-cell specific mitogens, as well as nucleotide sequences (which may further include an associated delivery vector) encoding for therapeutic agents having any one or combination of these therapeutic effects. Examples include plasmids that encode an antiproliferative protein within the arterial walls to help prevent a recurring blockage due to restenosis, anti-inflammatory proteins and anti-thrombotic polysaccharides designed to prevent blood clotting.

It is noted that multiple therapeutic agents can be used simultaneously in connection with the present invention. Moreover, even in embodiments centered on the use of high-molecular-weight therapeutic agents, the medical device may optionally contain other therapeutic agents that are suitable for localized delivery from implantable or insertable medical devices, even though these optional therapeutic agents are not high-molecular-weight therapeutic agents. Numerous examples of such other therapeutic agents are described above.

The amount of therapeutic agent that is provided in connection with the various embodiments of the present invention is readily determined by those of ordinary skill in the art and ultimately depends upon the condition to be treated, the nature of the therapeutic agent itself, the avenue by which the medical device is administered to the intended subject, and so forth.

In some embodiments of the present invention, the therapeutic agent is incorporated within a polymer layer provided as a coating on the medical device. The polymer layer hence acts as a depot for the therapeutic agent, releasing the therapeutic agent in a controlled manner once the medical device has been positioned within the patient's body.

In other embodiments, a polymer layer acts as a barrier layer to control the passage of the therapeutic agent. In such embodiments, the therapeutic agent is positioned under the barrier layer. As an example, the barrier layer can be disposed over a layer of therapeutic agent which has been disposed directly onto the surface of the medical device or onto the surface of a polymeric coating layer previously applied onto the surface of the medical device. As another example, the barrier layer can be disposed over a layer that contains a material in addition to the therapeutic agent, for example, a polymer matrix layer within which the therapeutic agent is incorporated.

Polymers appropriate for the practice of the present invention include a variety of biocompatible polymers known in the art to be suitable for use in implantable or insertable medical devices. The biocompatible polymer may be biostable or biodisintegrable. By "biostable" is meant a polymer that does not substantially disintegrate (i.e., deteriorate) in vivo. Thus, a biostable polymer is one that maintains its structural integrity, i.e., is substantially inert, in the presence of a physiological environment. "Biodisintegrable" polymers are those that undergo substantial deterioration in vivo, and include soluble polymers, bioerodable polymers and biodegradable polymers.

Exemplary biocompatible biostable polymers include numerous thermoplastic and elastomeric polymeric materials that are known in the art. Polyolefins such as metallocene catalyzed polyethylenes, polypropylenes, and polybutylenes and copolymers thereof; ethylenic polymers such as polystyrene; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); fluoropolymers such as polytetrafluoroethylene (PTFE); polyesters such as polyethylene terephthalate (PET); polyester-ethers; polysulfones; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing are non-limiting examples of biostable biocompatible polymers useful for manufacturing the medical devices of the present invention.

Additional exemplary biocompatible biostable polymers, which are not necessarily exclusive of those listed in the prior paragraph, are described in U.S. Pat. No. 6,153,252, the disclosure of which is incorporated by reference. These polymers include polyurethanes, silicones, poly(meth)acrylates, polyesters, polyalkylene oxides such as polyethylene oxide, polyvinyl alcohols, polyethylene glycols and polyvinyl pyrrolidone; hydrogels such as those formed from crosslinked polyvinyl pyrrolidone and polyesters could also be used. Other polymers include polyolefins, polyisobutylene and ethylene-alphaolefin copolymers; acrylic polymers (including methacrylic polymers) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as nylon 6,6 and polycaprolactam; alkyd resins; polycarbonates; polyoxymethylenes; polyimides; polyethers; epoxy resins; rayon; rayon-triacetate, cellulose, cellulose acetate, cellulose acetate butyrate; cellophane; cellulose nitrate; cellulose propionate; cellulose ethers (i.e. carboxymethyl cellulose and hydroxyalkyl celluloses); and combinations thereof. Polyamides for the purpose of this application would also include polyamides of the form —NH—$(CH_2)_n$—CO— and NH—$(CH_2)_x$—

NH—CO—(CH$_2$)$_y$—CO, wherein n is typically an integer in from 6 to 13; x is an integer in the range of form 6 to 12; and y is an integer in the range of from 4 to 16. Mixtures and block or random copolymers of any of the foregoing are also useful in the present invention.

Among particularly beneficial biostable polymeric materials are polyolefins, polyolefin-polyvinylaromatic copolymers including polystyrene-polyisobutylene copolymers and butadiene-styrene copolymers, ethylenic copolymers including ethylene vinyl acetate copolymers (EVA) and copolymers of ethylene with acrylic acid or methacrylic acid; elastomeric polyurethanes and polyurethane copolymers; metallocene catalyzed polyethylene (mPE), mPE copolymers; ionomers; polyester-ethers; polyamide-ethers; silicones; and mixtures and copolymers thereof.

Also among particularly beneficial biostable polymeric materials are block copolymers having at least two polymeric blocks A and B. Examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X—(BA)$_n$ (includes diblock, triblock and other radial block copolymers), where n is a positive whole number and X is an initiator molecule (also sometimes referred to as a starting seed molecule). One specific group of polymers have X-(AB)$_n$ structures, which are frequently referred to as diblock copolymers and triblock copolymers where n=1 and n=2, respectively (this terminology disregards the presence of the initiator molecule, for example, treating A-X-A as a single A block with the triblock therefore denoted as BAB). Where n=3 or more, these structures are commonly referred to as star-shaped block copolymers.

The A blocks are typically soft elastomeric components which are based upon one or more polyolefins, for example, a polyolefinic block having alternating quaternary and secondary carbons of the general formulation: —(CRR'—CH$_2$)$_n$—, where R and R' are linear or branched aliphatic groups such as substituted or unsubstituted methyl, ethyl, propyl, isopropyl, butyl, isobutyl and so forth, or substituted or unsubstituted cyclic aliphatic groups such as cyclohexane, cyclopentane, and the like. Specific examples include blocks of based on isobutylene,

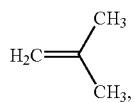

(i.e., polymers where R and R' are the same and are methyl groups) and blocks based on ethylene and butylene.

The B blocks are typically hard thermoplastic blocks that, when combined with the soft A blocks, are capable of, inter alia, altering or adjusting the hardness of the resulting copolymer to achieve a desired combination of qualities. Beneficial B blocks are polymers of methacrylates or polymers of vinyl aromatics. More beneficial B blocks are (a) made from monomers of styrene

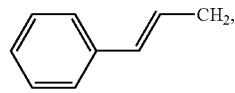

styrene derivatives (e.g., α-methylstyrene, ring-alkylated styrenes or ring-halogenated styrenes) or mixtures of the same or are (b) made from monomers of methylmethacrylate, ethylmethacrylate hydroxyethyl methacrylate or mixtures of the same.

Typical initiator molecules are those known in the art and include tert-ester, tert-ether, tert-hydroxyl or tert-halogen containing compounds, for example, cumyl esters of hydrocarbon acids, alkyl cumyl ethers, cumyl halides and cumyl hydroxyl compounds as well as hindered versions of the above.

Particular polymers within this category include (a) copolymers of polyisobutylene with polystyrene or polymethylstyrene, for example, polystyrene-polyisobutylene-polystyrene (SIBS) triblock copolymers; these polymers are described, for example, in U.S. Pat. No. 5,741,331, U.S. Pat. No. 4,946,899 and United States Patent Application 20020107330, each of which is hereby incorporated by reference in its entirety; and (b) a copolymer containing one or more blocks of polystyrene and one or more random blocks of ethylene and butylene, for example, a polystyrene-polyethylene/butylene-polystyrene (SEBS) copolymer, available as Kraton™ G series polymers available from Kraton Polymers.

Typical biodisintegrable polymers include, but are not limited to, polylactic acid, polyglycolic acid and copolymers and mixtures thereof such as poly(L-lactide) (PLLA), poly(D,L-lactide), polyglycolic acid (polyglycolide), poly(L-lactide-co-D,L-lactide), poly(L-lactide-co-glycolide), poly(D,L-lactide-co-glycolide), poly(glycolide-co-trimethylene carbonate), poly(D,L-lactide-co-caprolactone), poly(glycolide-co-caprolactone), polyethylene oxide (PEO), polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate and copolymers of polyhydroxybutyrate, poly(phosphazene), poly(phosphate ester), poly(amino acid) and poly(hydroxy butyrate), polydepsipeptides, maleic anhydride copolymers, polyphosphazenes, polyiminocarbonates, poly[(97.5% dimethyl-trimethylene carbonate)-co-(2.5% trimethylene carbonate)], cyanoacrylate, hydroxypropylmethylcellulose, polysaccharides such as hyaluronic acid, chitosan and regenerate cellulose, tyrosine-based polymers (e.g., tyrosine-derived polycarbonates such as the Tyrosorb™ Synthetic Polymers available from Integra LifeSciences and those described in U.S. Pat. No. 6,120,491), and proteins such as gelatin and collagen and genetically engineered variants thereof (e.g., collagen engineered to include thrombin cleavage sites), as well as mixtures and copolymers of the above, among others.

Additional biodisintegrable polymers, which are not necessarily exclusive of those listed in the prior paragraph, are described in U.S. Pat. No. 6,153,252, the disclosure of which is incorporated by reference. These polymers include aliphatic polyesters, poly(amino acids), copoly(ether-esters), polyalkylene oxalates, polyamides, poly(iminocarbonates), polyorthoesters, polyoxaesters, polyamidoesters, polyoxaesters containing amido groups, poly(anhydrides), polyphosphazenes, biomolecules, and blends thereof. For the purpose of this invention, aliphatic polyesters include homopolymers and copolymers of lactide (which includes lactic acid d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Among poly(iminocarbonate)s useful in the present invention include those described by Kemnitzer and Kohn, in the Handbook of Biodegradable Polymers, edited by Domb, Kost and Wisemen, Hardwood Academic Press, 1997, pages 251-272. Among copoly(ether-esters) useful in the present invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Among polyalkylene oxalates useful in the present invention include those described in U.S. Pat. Nos. 4,208,511; 4,141,087; 4,130,639; 4,140,678; 4,105,034; and 4,205,399 (incorporated by reference herein). Among polyphosphazenes, co-, ter- and higher order mixed monomer based polymers made from L-lactide, D,L-lactide, lactic acid, glycolide, glycolic acid, para-dioxanone, trimethylene carbonate and epsilon-caprolactone useful in the present invention include those described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons are also useful in the present invention. Among polyoxaesters, polyoxaamides and polyoxaesters containing amines and/or amido groups useful in the present invention include those described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583 (which are incorporated herein by reference). Polyorthoesters include those described by Heller in Handbook of Biodegradable Polymers, edited by Domb, Kost and Wisemen, Hardwood Academic Press, 1997, pages 99-118 (hereby incorporated herein by reference). Biodisintegrable polymers also include naturally occurring materials that may be enzymatically degraded in the human body or are hydrolytically unstable in the human body such as fibrin, fibrinogen, collagen, elastin, and absorbable biocompatible polysaccharides such as chitosan, starch, fatty acids (and esters thereof), glucoso-glycans and hyaluronic acid. Mixtures and block or random copolymers of any of the foregoing are also contemplated.

A layer of the polymer can be provided upon the medical device using essentially any technique known in the art. For example, where the polymer can be applied as a liquid (e.g., where monomer is applied as a liquid and subsequently polymerized; where the polymer is dissolved or dispersed in a solvent or carrier liquid and the solvent or carrier liquid subsequently removed; or, where the polymer is a thermoplastic material that can be heated to above its melting point, applied and subsequently cooled), a number of techniques are available for application, including casting, spin coating, web coating, spray coating, dip coating, fluidized bed coating, positive displacement coating, ink jet techniques and so forth. Where the polymer is of a thermoplastic character, a variety of additional standard thermoplastic processing techniques can also be used including compression molding, injection molding, blow molding, spinning, vacuum forming and calendaring, as well as extrusion.

In general, it is desirable to control the release of the therapeutic agent from the medical device such that therapeutic agent remains available for release after the device is fully deployed at the treatment site. This typically means that no more than about 50%, and more typically no more than about 10%, of the therapeutic agent is released prior to full deployment of the medical device.

For restenosis treatment, it is desirable that the release be initiated before or at the time at which cell proliferation occurs, which generally begins approximately three days after the injury to the artery wall by the PTCA procedure. Of course, the release profile will be tailored to the condition that is being treated. For example, where an anti-inflammatory or anti-thrombotic effect is desired, release is typically initiated sooner. Moreover, in instances where DNA is used that has an expression half-life that is shorter than the time period desired for administration of the therapy, release of the DNA from the device is typically regulated such that it occurs over a time period longer than the half-life of the DNA expression, thus allowing new copies of DNA to be introduced over time and thereby extending the time of gene expression.

The performance of the medical devices of the invention can be evaluated in vitro in a number of ways, including investigation of the release kinetics of the therapeutic agent, as well as the integrity of the therapeutic agent that is released. For instance, in the case where the therapeutic agent is a high-molecular-weight therapeutic agent such as DNA, the conformational and structural integrity of the DNA can be investigated.

In many embodiments of the invention, high-molecular-weight therapeutic agents are incorporated during the processing of the polymer material that forms a coating on a surface of the medical device. However, the therapeutic agents may not be stable under the conditions required for such processing. For instance, high-molecular-weight therapeutic agents such as polynucleotides and polypeptides, and especially polynucleotides in the form of plasmid DNA, may be subjected to substantial shear stresses when they are mixed with a polymer and applied to a medical device as described above. This is especially true where an organic solvent is used to process the polymer. In these cases, polynucleotides such as plasmid DNA are commonly insoluble in these organic solvents. Although water/oil emulsions can be prepared to facilitate dispersion of the plasmid DNA, the use of high speed mechanical mixing to achieve effective emulsification can result in shearing of the polynucleotide, ultimately reducing transfection efficiency.

In accordance with certain embodiments of the present invention, this obstacle is addressed by first precipitating or depositing the polynucleotide (or other high-molecular-weight therapeutic agent) on the surface of the medical device. Subsequently, a polymeric barrier layer is provided over the polynucleotide layer. In this way, shear stresses upon the polynucleotide can be controlled, and the release of the polynucleotide can be regulated. The rate of release of the active polynucleotide can be controlled by the type and construction of the polymeric barrier layer. At the same time, the polynucleotide is protected by the polymer from rapid degradation within the patient.

Various methods are available for forming a precipitated layer of polynucleotide upon the medical device. For example, a solution of the polynucleotide can first be provided. Then, the medical article can be dipped into the polynucleotide solution, followed by drying. Alternatively, the polynucleotide solution can be applied to the medical article by other coating techniques such as those previously discussed (e.g., solvent casting, spin coating, web coating, spray coating, fluidized bed coating, positive displacement coating, and ink jet techniques), so long as the shear stresses are kept to tolerable levels. Dipping the medical device in an aqueous solution of polynucleotide is an example of a method of forming the precipitated layer.

The precipitated layer of polynucleotide is subsequently covered with a layer of polymer, such as those discussed above, which acts as a barrier for the release of the polynucleotide. The polymer layer can be applied using any of the coating techniques previously discussed and can either be biostable, in which case the polynucleotide will be transported through the layer, or biodisintegrable, in which case the polynucleotide is released by transport through the layer, by disintegration (e.g., biodegradation, bioerosion and/or dissolution) of the layer, or both.

Regardless of whether the therapeutic agent is disposed within the polymer or whether the polymer acts as a barrier layer, it may be difficult in some instances to achieve adequate transport of the therapeutic agent through the polymer to effect significant release, especially where the therapeutic agent is a high-molecular-weight therapeutic agent. For example, this difficulty is observed on occasion for various biostable polymers, including block copolymers comprising polymer blocks of olefin molecules and polymer blocks of vinyl aromatic molecules, for example, block copolymers of polyisobutylene and polystyrene (or of polyisobutylene and polystyrene derivatives such as poly α-methylstyrene).

In certain embodiments of the present invention, these transport issues are addressed by combining the polymer with a removable material. Without wishing to be bound by theory, it is believed that, by providing a removable material according to the above embodiments of the invention, a more porous polymer is provided, increasing the transport of high-molecular-weight therapeutic agent through the polymer.

In some embodiments, the removable materials are leachable materials (i.e., materials that can be extracted by exposure to a solvent or other agent that causes removal of the leachable material). In these embodiments, the leachable material and the polymer are combined and associated with the medical device, typically by applying the combination to the medical device surface. Subsequently, the leachable material is removed either in vitro (i.e., before insertion or implantation) or in vivo (i.e., after insertion or implantation). Where the leachable material is removed in vitro, the solvent may be selected such that the leachable material is removed from the polymer, while the high-molecular-weight therapeutic agent that is present is not substantially removed (for example, in the case where DNA is selected as the therapeutic agent, a leachable material can be selected that is removable upon solvent exposure, while the DNA remains undissolved in the solvent). The leachable material can be removed in vivo for example, upon exposure of the leachable material to a physiological fluid, which dissolves, erodes or degrades the leachable material.

For example, the polymer may comprise a biostable polymer having regions of leachable material dispersed therein. The leachable material can be removed from the remaining bulk of biostable polymer by mechanisms such as dissolution, erosion or degradation. It is also effective to utilize a biodisintegrable polymer having leachable regions dispersed therein, so long as the time frame within which the leachable regions are removed is substantially shorter than the time frame within which the remaining bulk of the polymer disintegrates. These regions will, therefore, degrade more quickly, providing, as discussed below, means to increase transport of the high-molecular-weight therapeutic agent through the remaining biodisintegrable polymer.

Typical leachable materials include the following: polyethylene glycol (also known as polyoxyethylene), polyalkylene oxides including polyethylene oxide and polyethylene oxide/polypropylene oxide copolymers (also known as poloxamers), polyhydroxyethylmethacrylate, polyvinylpyrrolidone, polyacrylamide and its copolymers, polylactides, polyglycolides, polyanhydrides, polyorthoesters and their copolymers, proteins including albumin, peptides, liposomes, cationic lipids, ionic or nonionic detergents, salts including potassium chloride, sodium chloride and calcium chloride, sugars including galactose, glucose and sucrose, polysaccharides including soluble celluloses, heparin, cyclodextrins and dextran, and blends of the same. Further leachable materials can be found among the biodisintegrable polymers listed above.

Where a polynucleotide is used as the high-molecular-weight therapeutic agent, leachable components that are further known to improve transfection efficacy, such as polyalkylene oxides, cationic lipids, liposomes and cyclodextrins, are particularly beneficial.

Moreover where the polymer that is selected contains hydrophobic elements, for example, biostable copolymers having blocks of polyisobutylene and polystyrene, the leachable component is ideally amphiphilic to assist with the formulation of the polymer (e.g., where an water-in-oil or oil-in-water emulsion is formed during formulation). Typical amphiphilic leachable components include polyalkylene oxides and ionic or nonionic detergents.

Thus, leachable components such as polyalkylene oxides are particularly beneficial for the practice of the invention, because they can (1) like other leachable components, enhance therapeutic agent transport upon deployment of the medical device, (2) provide stable emulsions due to their amphiphilic properties, particularly during matrix formation with polymers containing hydrophobic elements, and (3) enhance cellular uptake of polynucleotides due to their transfection-enhancing characteristics.

In other embodiments, the removable materials are evaporable. In some of these embodiments, the evaporable materials may comprise evaporable salts such as ammonium salts (e.g., ammonium bicarbonate). Alternatively, they may comprise the oil phase and/or the water phase in a water-in-oil or oil-in-water emulsion of the polymer and the high-molecular-weight therapeutic agent. Typical emulsifying agents for this purpose include polyalkylene oxides and detergents. Typical oil phase materials include toluene, tetrahydrofuran, butyl acetate, chloroform, and methylene chloride. In this embodiment, the emulsion is typically applied to a surface of the medical device, after which the volatile or evaporable phases (typically the water and oil) are removed, for example, by applying heat under vacuum conditions. It is also noted that, in many instances, the emulsifying agent will also elute from the polymer once the medical device is inserted or implanted as discussed above, removing further material from the polymer. Moreover, where a polynucleotide is used as the high-molecular-weight therapeutic agent, emulsifying agents that are also known to improve transfection efficacy, such as polyalkylene oxides and cationic lipids, are particularly beneficial.

In general, it is desirable to tailor the release profile of therapeutic agent from the medical devices of the present invention. According to certain embodiments of the invention, release can be tailored by providing a medical device that has a multi-layer coating covering at least a portion of the medical device. The multi-layer coating includes: (a) one or more therapeutic agent containing layers and (b) one or more polymeric layers. The one or more polymeric layers provide a polymer composition gradient in a direction normal to the surface of the coating (i.e., a gradient in the polymer composition is observed as one proceeds deeper into the coating).

Although these embodiments may be used with all sizes of therapeutic agents, high-molecular-weight therapeutic agents are particularly beneficial.

Such a polymer composition gradient can be provided in a number of ways. As an example, a single polymeric layer can be provided, which has a composition gradient over its thickness. As another example, multiple polymeric layers of differing composition can be disposed over one another to collectively provide a polymer composition gradient in a direction normal to the surface of the coating.

In some embodiments, the therapeutic agent containing layers are disposed beneath the polymeric layers. In other embodiments, the therapeutic agent containing layers are interspersed between the polymeric layers, typically in an alternating configuration. In either case, the therapeutic agent release profile that is associated with the medical device is shaped by the composition gradient that is established within the polymeric portion of the multi-layer coating. Moreover, the therapeutic agent release profile can be tuned by varying the shape of this gradient.

One way to establish a polymer layer composition gradient is to vary the composition of the polymer material itself. For example, the relative amounts of two or more monomers within a copolymer can be varied to establish such a gradient. Alternatively, the relative amounts of two or more polymers (including copolymers) within a polymer blend can be varied.

As a specific example, the relative amounts of a hydrophobic polymer (for example, a polystyrene-polyisobutylene copolymer such as the polystyrene-polyisobutylene-polystyrene block copolymers discussed above) and a hydrophilic polymer (for example, a styrene-ethyleneoxide copolymer such as a polystyrene-polyethylene oxide-polystyrene triblock copolymer) can be varied within a polymer blend to create a hydrophobicity gradient within the coating.

As a more specific example, a layer containing a hydrophilic therapeutic agent such as plasmid DNA is deposited on a medical device such as a stent. Subsequently, multiple layers, each containing a blend of hydrophilic and hydrophobic polymers, are deposited over the therapeutic agent-containing layer. The innermost deposited layer is provided with the greatest relative amount of hydrophobic polymer, with each subsequently deposited layer containing higher and higher relative amounts of hydrophilic polymer. As a result, a hydrophobicity gradient is established.

Conversely, with a hydrophobic therapeutic agent such as paclitaxel, the innermost layer is provided with the greatest relative amount of hydrophilic polymer, with subsequent layers containing relatively greater amounts of hydrophobic polymer.

Another way to establish a polymer layer composition gradient is to vary the porosity within the polymer layers. Polymer porosity can be established, for example, during the course of polymer formation or subsequent to polymer formation. For example, polymer porosity can be established by providing the polymer with a removable component, such as those discussed above. Upon removal of the removable component (e.g., either in vitro or in vivo), a porous structure is established. (As discussed further below, where the leachable component is dissolved upon implantation or insertion of the medical device in vivo, an osmotic gradient is also established, which can also influence therapeutic agent release.)

Another way to establish a polymer layer composition gradient is to vary the concentration of one or more additional species the polymer layers. For example, by varying the concentration of an acidic or basic species within the one or more polymer layers, a pH gradient can be provided. Examples of basic and acidic species include polylysine polymers and polyacrylic acids (e.g., carbopol).

As another example, an osmotic gradient can be provided by varying the concentration of a soluble species within the one or more polymer layers. Examples of soluble species include the soluble leachable species listed above.

As another example, a charge gradient can be provided by varying the concentration of an ionic species within the one or more polymer layers. Examples of ionic species for this purpose include potassium metaphosphates.

In many embodiments of the present invention, it is desirable to apply a polymer to an expandable medical device, such as a stent or a balloon catheter, for example, by providing a coating of the polymer on the device. This can occur, for example, in the case where a high-molecular-weight therapeutic agent is disposed within the polymer (i.e., within a polymer matrix) or where the polymer acts as a barrier layer for a high-molecular-weight therapeutic agent. With many polymer materials, however, polymer cracking can occur upon expansion of the medical device. Moreover, where large amounts of polymer coating are used (e.g., in response to the need for large amounts of therapeutic agent), cracking difficulties upon implantation or insertion of the medical device can be exacerbated.

To address such issues, the polymer in some embodiments of the invention is admixed with a plasticizer to improve the polymer's resistance to cracking, thus avoiding, for example, uncontrolled release, embolism risks and unsuccessful therapeutic outcomes.

The plasticizer can also be selected to modify the rate at which the high-molecular-weight therapeutic agent is released from the polymer, for example, by influencing the diffusivity of the high-molecular-weight therapeutic agent within the polymer or by influencing the degradation rate of a biodisintegrable polymer.

Typical plasticizers include for example: glycerol (glycerin USP), triacetyl glycerin (triacetin), ethylene glycol, triethylene glycol, polyethylene glycol, propylene glycol, polyalkylene oxides including polyethylene oxide and polyethylene oxide/polypropylene oxide copolymers, citric acid esters, sebacic acid esters, phthalic acid esters, silicone fluids, and analogs and derivatives and mixtures thereof.

In some embodiments, the plasticizer functions both to provide resistance to cracking of the polymer and as a leachable material, which as discussed above is believed to provide a more porous polymer network, facilitating transfer of the high-molecular-weight therapeutic agent through the polymer. Examples of plasticizers that provide this dual functionality include, but are not limited to, ethylene glycol, triethylene glycol, polyethylene glycol, propylene glycol, polyalkylene oxides including polyethylene oxide and polyethylene oxide/polypropylene oxide copolymers.

Where a polynucleotide is used as the high-molecular-weight therapeutic agent, plasticizers that are also known to improve transfection efficacy, such as polyalkylene oxides and cationic lipids, are particularly beneficial.

EXAMPLES

Example 1

Materials

Biodisintegrable polymers: (a) poly(lactic-co-glycolic acid) (50 mol % lactic acid-50 mol % glycolic acid) having acid end groups available from MediSorb, hereinafter referred to as "PLGA (acid end groups)", (b) low molecular weight poly(lactic-co-glycolic acid) (50 mol % lactic acid-50 mol % glycolic acid) available from MediSorb, hereinafter referred to as "PLGA (low molecular weight), (c) collagen type I (available from Sigma), (d) gelatin type A (available from Sigma), (e) gelatin type B (available from Sigma), and (f) hyaluronic acid (available from Anika Therapeutics) (HA).

Plasticizers: (a) triacetin (Sigma), (b) sebacic acid dibutyl ester (Sigma), (c) glycerol (Sigma), (d) polyethylene glycol 3350 (PEG) (Union Carbide) and (f) silicon oil (Dow Corning).

A 4-kilobase reporter plasmid pNGVL2 (University of Michigan) encoding beta-galactosidase was isolated by cationic affinity chromatography and purified by CsCl gradient centrifugation for use herein.

Example 2

Stent Coating

PLGA (low molecular weight) and PLGA (acid end groups) were homogenized (2 minutes, highest level) separately into a stable emulsion with plasmid DNA (18.6 mg/ml) in a (3:1) (mg:ul) ratio. NIR stents (7/9 mm) were dipped into the two different solutions for 15 seconds and then spun to remove excess coating from the windows of the stent. The coated stents were then dried in a vacuum oven at 40° C. overnight before testing.

Collagen was formulated with poly(acrylic acid) (PAA) (available from Aldrich) as a model for DNA (10 mg/ml) in a (5:1) (mg:mg) ratio and sprayed onto the stent. The spraying parameters were then adjusted to produce the optimal level of coating.

Stents were coated with both types of gelatin in the same procedure as collagen. In addition, the glycerol and PEG plasticizers were used in the formulation at different concentrations (5 to 30 wt/o for the PEG and 12.5 to 25 wt % for the glycerol) to help prevent cracking.

Stents were coated with hyaluronic acid in the same procedure as collagen. The plasticizers PEG, triacetin, sebacic acid dibutyl ester, and polyethylene glycol 3350 (PEG) were used in the formulation to determine their effect on cracking, and the formulation with the best properties was used to encapsulate DNA. For example, 22 wt % silicon oil (Si) and 78 wt % hyaluronic acid (HA) are first homogenized for five minutes into a stable emulsion. An Si-HA:DNA emulsion is then made by adding DNA (typically 18.6 mg/ml) in a (1:1) (mg:ul) ratio homogenizing for two additional minutes. Stents were dipped for 10 seconds and spun at a high rpm to remove excess coating. (1:1) (mg:ul) HA:DNA samples were also made by homogenizing for two minutes at the highest level and then following the same dipping and spinning procedure as above.

Example 3

Conformational Analysis of Released DNA

Released DNA was assessed through 1% agarose gel electrophoresis (70 V, 1 h) in the presence of ethidium bromide and compared to un-encapsulated plasmid DNA to determine the structural integrity and purity of released DNA.

Example 4

Analysis of Coating Solubility and DNA release

The various coatings were evaluated for solubility by dipping the coated stents in PBS with a pH of 7.4 for predetermined intervals, and by measuring the amount of coating dissolved during each time span. Similarly, in vitro release of plasmid DNA was evaluated for each stent by immersing the stent in PBS of 7.4 pH, and by measuring the concentration of released plasmid DNA in the solution at 280 nm.

Example 5

Evaluation of Coating Mechanical Integrity

The mechanical integrity of the coatings was evaluated by viewing the stents under an optical microscope to determine the extent of webbing over windows of the stent, and by viewing the coating under a scanning electron microscope (SEM) to determine cracking and surface characteristics of the polymer before and after expansion of the stent.

Example 6

Mechanical Integrity of Coating, DNA Release and DNA Integrity Associated with PLGA Polymers Table 1 shows the ratio PLGA to DNA for several stent samples. Table 1 also shows the average coating weight for the coating of the polymer on a stent, which is representative of the thickness of the coating, and indicates whether the coating cracked or not when the stent was expanded.

Under optical microscopy, stents coated from both types of PLGA were shown to exhibit webbing and filled windows. However, PLGA (acid end groups) has approximately twice the amount of coating by weight on the stent than PLGA (low molecular weight) as seen from Table 1 below. When analyzed by SEM, PLGA (acid end groups) did not crack upon expansion of the stent even when the windows were filled with the polymer. However, PLGA (low molecular weight) does exhibit cracking upon expansion of the stent when analyzed by SEM.

TABLE 1

| | Characteristics of PLGA | | | |
|---|---|---|---|---|
| | PLGA:DNA Ratio | Ave. Coating Weight | # of Samples | Cracking |
| PLGA (low molecular weight) | (3:1) | 2500 μg | 3 | Yes |
| PLGA (acid end groups) | (3:1) | 4700 μg | 3 | No |
| PLGA (acid end groups) | (1:1) | 3500 μg | 3 | No |

Figure 4:
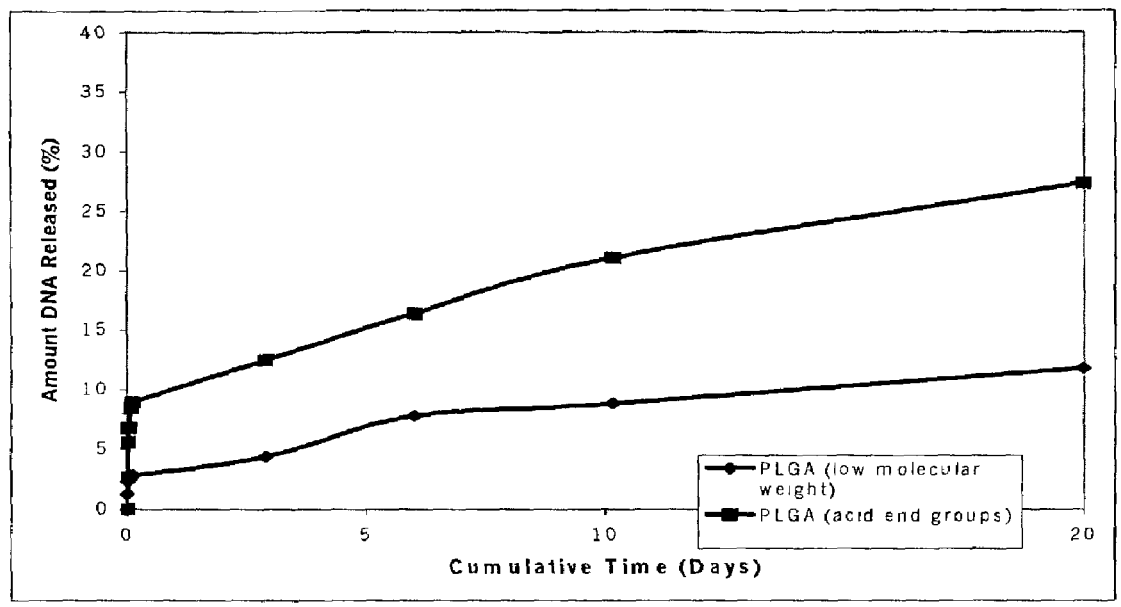
FIG. 4 is a graph of DNA release as a function of time for biodisintegrable coatings, according to an embodiment of the invention.
Figure 5:
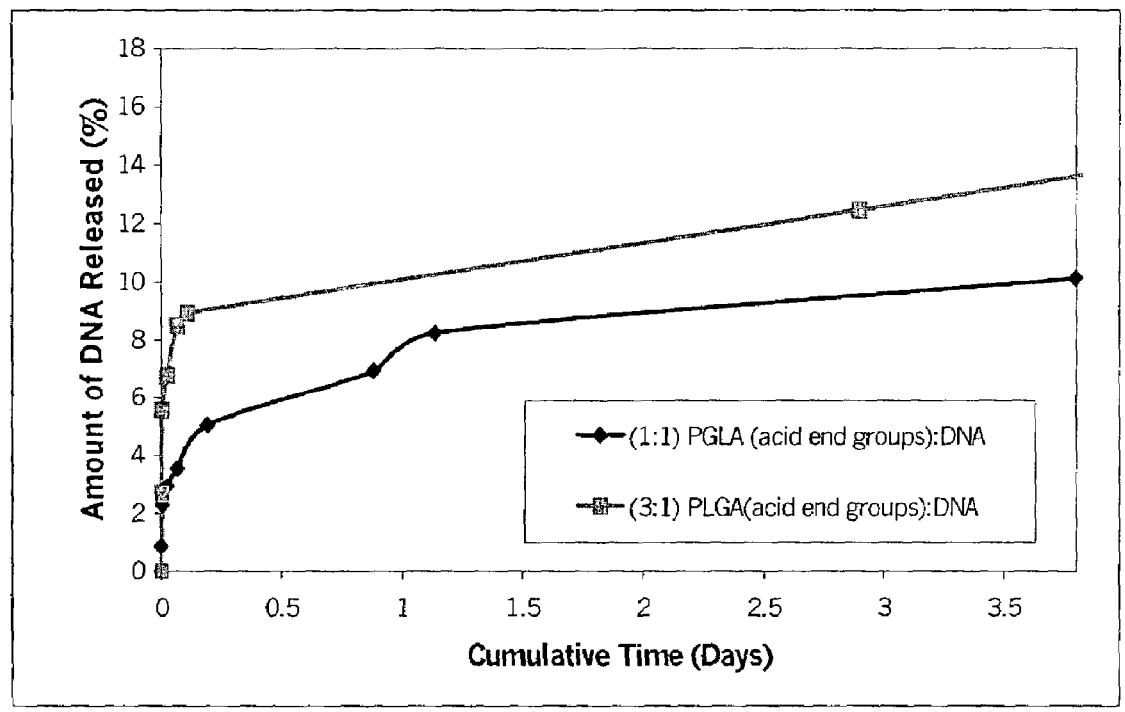
FIG. 5 is a graph of DNA release as a function of time for biodisintegrable coatings, according to an embodiment of the invention.

DNA release curves were generated from the release kinetics of DNA from stents coated with both types of PLGA (presented in FIGS. 4 and 5 with two different time scales). The percent cumulative release of PLGA (acid end groups) was significantly higher than PLGA (low molecular weight) at all time points. More than 25% of the plasmid DNA within the PLGA (acid ends groups) was released within 20 days, while PLGA (low molecular weight) only released 12% within that same time period. Both types of PLGA show a burst of release of DNA within the first two hours. 1 µg Contrary to what was expected, the percent cumulative release rate of (3:1) PLGA:DNA coated samples was higher than the (1:1) PLGA:DNA coated samples (FIG. 5). This could be due to the initial burst of DNA release within the first few minutes for the (3:1) PLGA:DNA samples. Also, the amount of coating achieved on the stents was less for the (1:1) samples than the (3:1) samples, as there was less plugging of the windows of the stent. SEM pictures of released stents show that most of the PLGA coating has been removed from the stent after approximately 70 days, and only some residual coating remains.

Plasmid DNA released from both types of PLGA was analyzed to determine the conformation of the DNA. The control plasmid DNA was primarily in supercoiled form (4 kb band) while the released PLGA/DNA shows conversion to the open circular form (6 kb band). The bands formed from the PLGA/DNA samples are low in intensity.

Example 7

Mechanical Integrity of Coating, DNA Release and DNA Integrity Associated with Gelatin, Collagen and Hyaluronic Acid Polymers A summary of the characteristics for the additional biodisintegrable polymers is shown in Table 2. Table 2 indicates the average coating weight for various combinations, whether the coating cracked upon expansion of the stent, and the average dissolution rate for certain of the combinations.

TABLE 2

Characteristics of Additional Polymers

| Polymer | Ave. Coating Weight | Cracking | Ave. Dissolution Rate |
|---|---|---|---|
| Hyaluronic Acid (HA) | 300 µg | Yes | 8 µg/min |
| Gelatin Type B | 500 µg | Yes | 43 µg/min |
| Gelatin Type A | 350 µg | Yes | 44 µg/min |
| Collagen Type I | 650 µg | Yes | 43 µg/min |
| Gel B w/ 12.5% Glycerol | 2000 µg | No | |
| Gel B w/ 22% Glycerol | 700 µg | No | |
| HA w/ 5% PEG | 1000 µg | Some | |
| HA w/ 10% PEG | 1600 µg | Some | |
| HA w/ 10% Si | 450 µg | No | |
| HA w/ 22% Si | 700 µg | No | |
| HA w/ 30% Si | 700 µg | No | |
| Si-HA:DNA | 1300 µg | No | |
| HA-DNA | 150 µg | Yes | |

A significant amount of collagen coating was achieved upon the stent-typically greater than the amount of coatings for the other polymers without plasticizer. Collagen was found to have a high solubility, and initial formulations of collagen with PAA resulted in the precipitation of PAA. Stents coated with this polymer also exhibited extensive cracking upon expansion.

Both types of gelatin exhibited moderately high solubility, a high initial degradation rate and cracking upon expansion of the stent. PAA was also shown to precipitate readily from formulations with gelatin type A.

Figure 6:
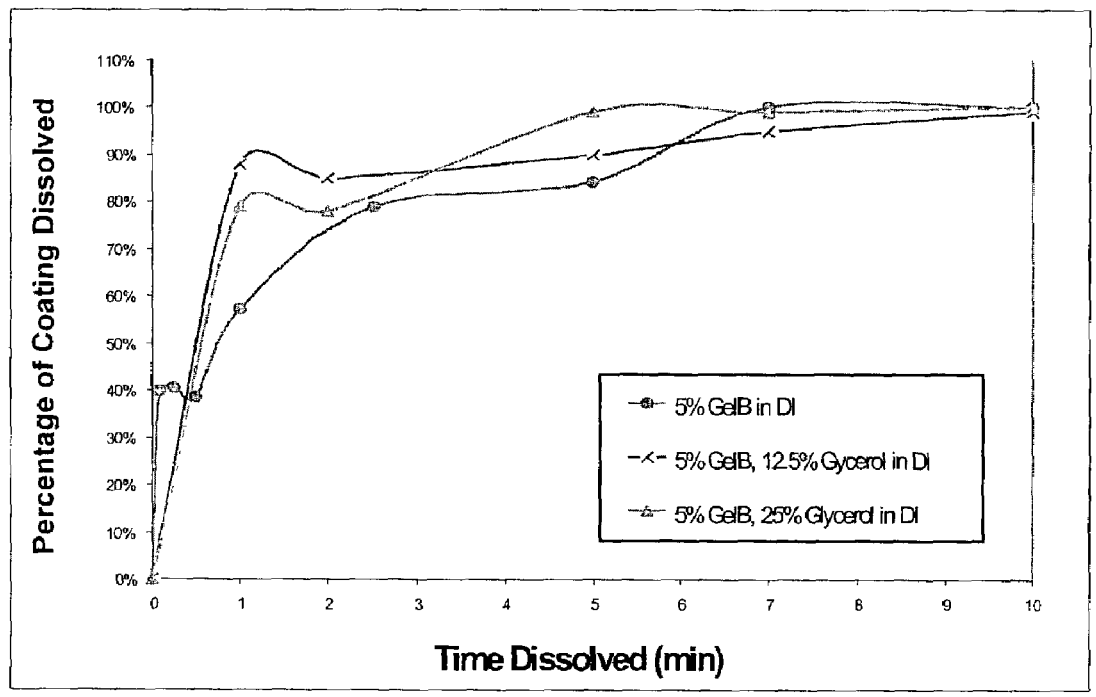
FIG. 6 is a graph of coating dissolution as a function of time for biodisintegrable coatings, according to an embodiment of the invention.

Incorporation of glycerol as a plasticizer into both types of gelatin resulted in the elimination of cracking of the polymer coating, as seen from SEM photographs and also resulted in a 400% increase in the amount of coating on the stent. With this addition, some increase in the solubility of gelatin in PBS can be seen (FIG. 6). There is a initial burst of dissolution within the first 1½ minutes, where at least 80% of the coating with the addition of glycerol is dissolved, as opposed to just 60% of pure gelatin type B, making glycerol an unattractive plasticizer for certain longer-term applications.

PEG was found to separate out of solution when combined with gelatin, and was not pursued further.

Figure 7:
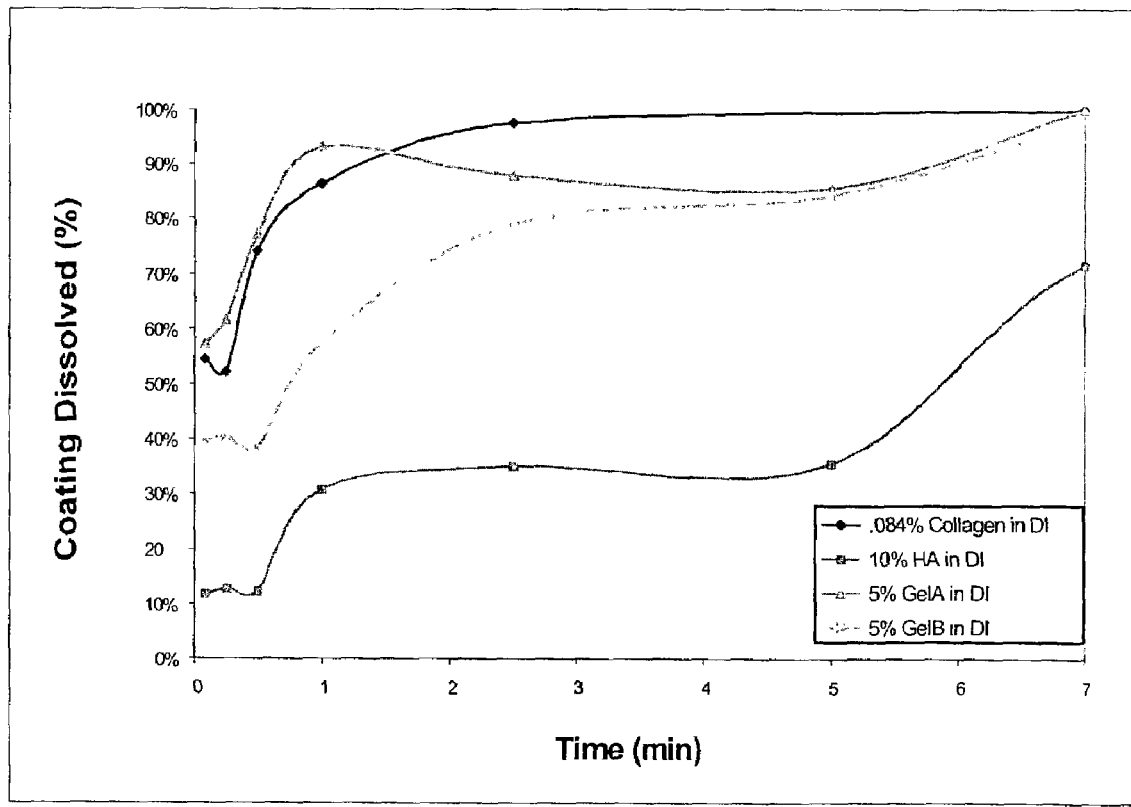
FIG. 7 is a graph of coating dissolution as a function of time for biodisintegrable coatings, according to an embodiment of the invention.

Turning now to hyaluronic acid, the generated solubility curves of FIG. 7 indicate that hyaluronic acid coatings have a lower solubility than coatings of both types of gelatin and collagen.

Studies of hyaluronic acid with the plasticizers triacetin and sebacic acid dibutyl ester showed that, even if the solution is homogenized into an emulsion, the plasticizers separate out of solution within one-half hour. The plasticizer PEG was found to be stable in solution however, and to greatly reduce the amount of cracking of the polymer coated stent when viewed by SEM, as well as increase the amount of coating on the stent by up to 500% (see Table 2). Incorporation of silicon oil (Si) into the hyaluronic acid plasticizer helped to eliminate cracking of the polymer-coated stent when viewed by SEM, and to increase the amount of coating achieved upon the stent by over 200% (Table 2).

Figure 8:
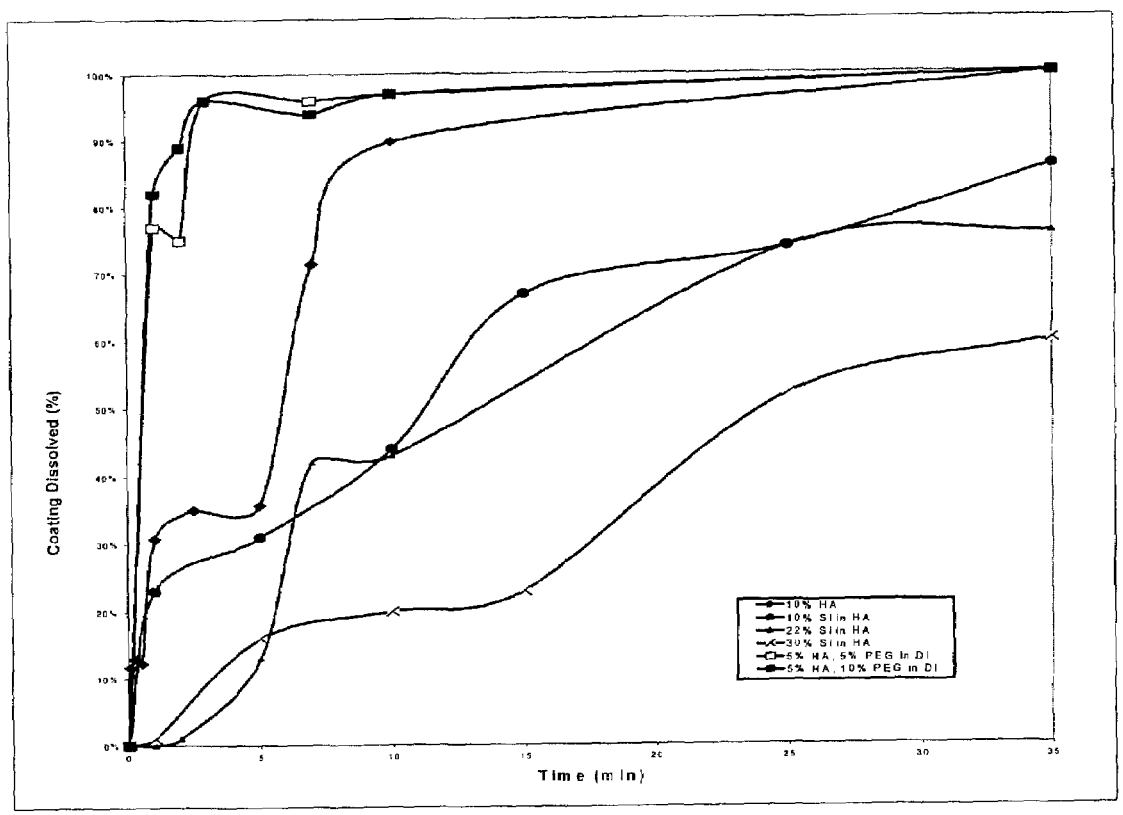
FIG. 8 is a graph of coating dissolution as a function of time for biodisintegrable coatings, according to an embodiment of the invention.

Solubility tests PBS indicate that PEG, presumably because it is a hydrophilic compound, increases the solubility of hyaluronic acid. FIG. 8 shows that there is a 95% initial burst phase of dissolution within the first five minutes where PEG is used. Almost all of the PEG/HA coating is dissolved within the first four minutes as compared to only 35% of a pure hyaluronic acid sample. On the other hand, solubility tests of hyaluronic acid and silicon oil show that the incorporation of silicon lowers the solubility of hyaluronic acid. There is a direct correlation between the increase in concentration of silicon oil and decrease in solubility of hyaluronic acid.

Only approximately 150 µg of coating was achieved on the HA/DNA coated stents, while the Si-HA/DNA samples had an average of 1300 µg (Table 2). SEM photographs show a uniform coating for both types of DNA containing polymers upon the stent. It was also found that essentially no cracking occurs upon expansion of stents coated with Si-HA/DNA, while stents coated with HA/DNA show cracking both before and after (to a greater extent) expansion.

Figure 9:
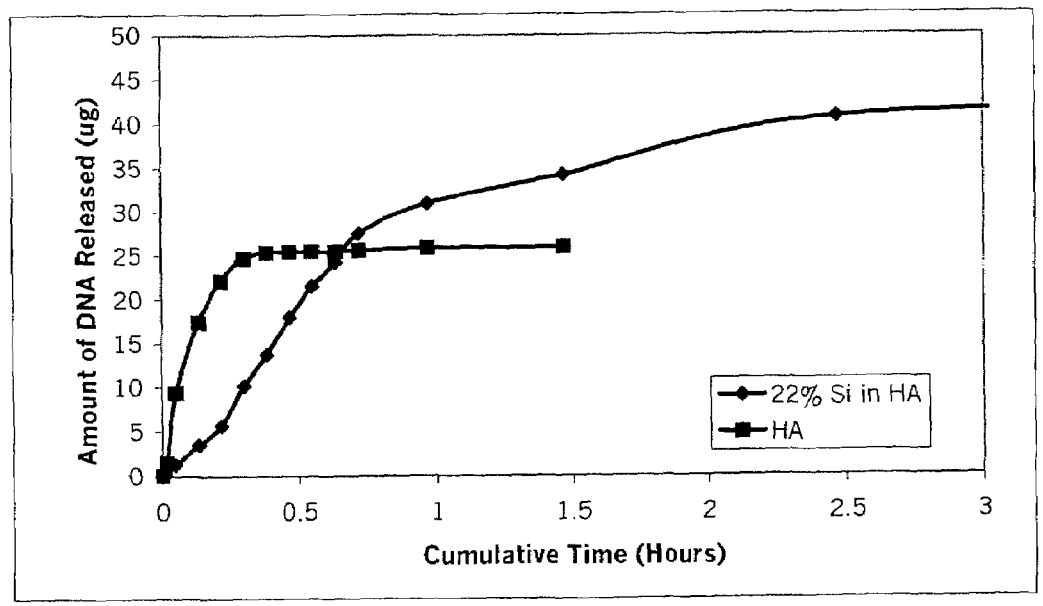
FIG. 9 is a graph of DNA release as a function of time for biodisintegrable coatings, according to an embodiment of the invention.
Figure 10:
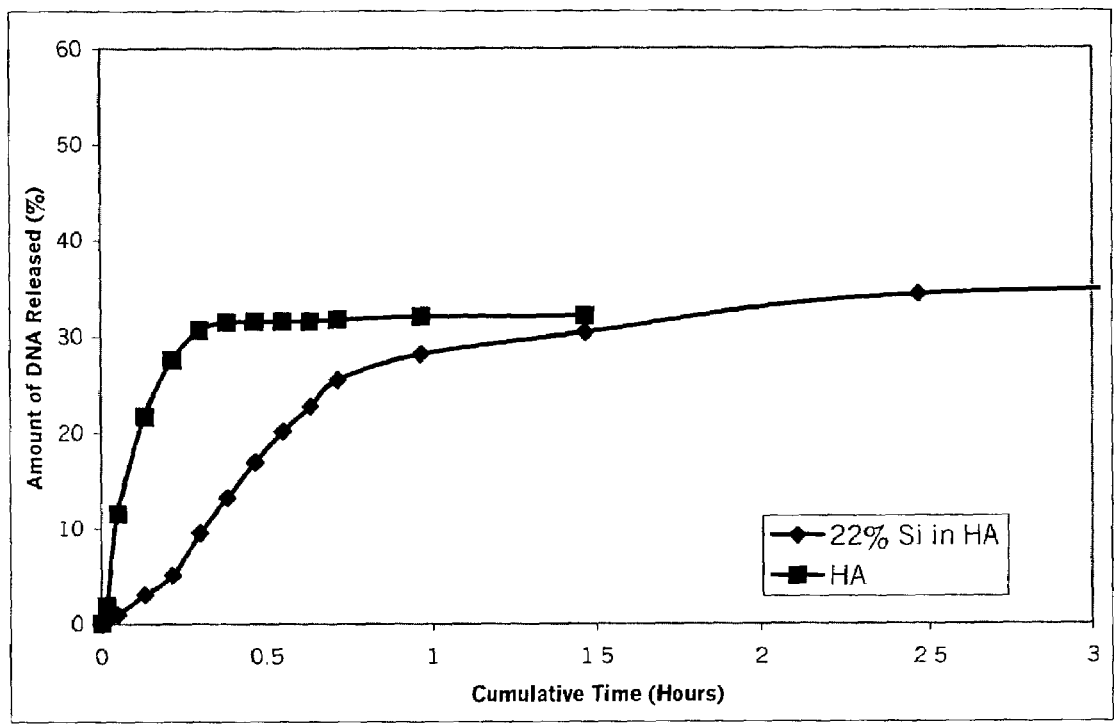
FIG. 10 is a graph of DNA release as a function of time for biodisintegrable coatings, according to an embodiment of the invention.

DNA release curves (FIG. 9) of hyaluronic acid show that most of the DNA, over 25 µg, is released within 20 minutes. The Si-HA samples show a 30 µg cumulative release during the first 45 minutes, followed by a gradual elution of up to 46 µg cumulative release over a period of 1½ days. In terms of DNA release in percentages, both HA and Si-HA samples release up to approximately 35%, but the HA samples release this amount twenty-three times faster than the Si-HA samples, with more than 22% released within the first five minutes (FIG. 10). SEM analysis and the mass weight of released samples indicate that some coating remains on the Si-HA stent even after the stent stops releasing DNA.

Hence, coatings for a stent containing HA (which is a biocompatible, non-toxic polymer) can be used to release plasmid DNA in a controlled and sustained manner. Since the coating fully dissolves within a few days, no residual coating is left on the stent after delivery of the plasmid DNA. As shown in FIG. 9, coatings containing silicon, HA and DNA release the bulk of DNA between five minutes to an hour and a half after insertion. The silicon and HA polymer coating also allows a large increase in the amount of coating on the stent, without clogging of the stent windows or cracking of the polymer film.

The DNA samples released from the HA and Si-HA coated stents show two bands, possibly three, of unequal intensity upon the gel. For the Si-HA samples, the lower band corresponds to the original pure supercoiled form of DNA (4 kb), while the more intense band (6 kb) corresponds to the nicked, open circular form of DNA, suggesting that the majority of the DNA is in the nicked, open circular form. A possible, very faint third band also seems to be apparent on the gel that could represent the linear, degraded form of DNA. The presence of the less desirable open circular form of the DNA is apparently due to homogenization of the mixture, during which the large plasmid molecules is mechanically sheared into the smaller molecules.

The HA-DNA samples show two bands of equal intensity corresponding to the supercoiled and open circular form of DNA, suggesting a roughly equal concentration of both forms. Similarly, a third band corresponding to the linear form of DNA might be represented on the gel. In both types of HA samples, intensity of the band corresponds positively to the concentration of DNA present in the released samples.

Example 8

Precipitation of DNA onto a Stent

For this example, stents were immersed in vials of DNA solutions (0.04 to 4.9 mg DNA/ml deionized water) and stored at −20° C. overnight. The vials were slowly brought to room temperature and stents were removed. Stents were placed on the mandrels and dried for 1 hour at 37° C.

Figure 11:
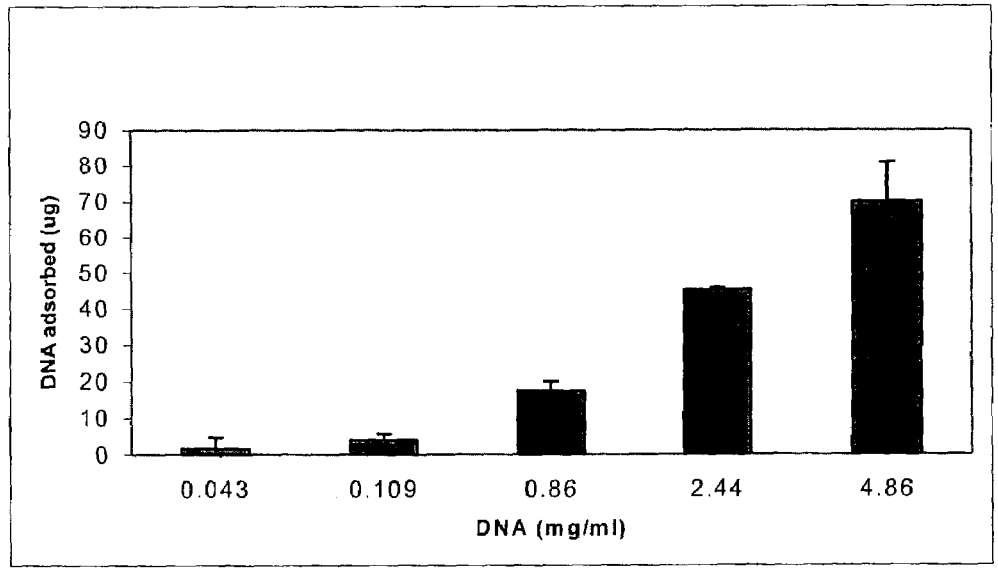
FIG. 11 is a graph of DNA adsorption as a function of DNA concentration, according to an embodiment of the invention.

From FIG. 11, it is seen that by increasing the concentration of DNA in the starting solution, the amount of DNA that is adsorbed to the stent likewise increases in a predictable manner.

Example 9

Polymer Overcoats

DNA coatings were prepared as described above in Example 8 (4.8 mg/ml DNA solution was used for this procedure). DNA films covered the stent windows and remained intact after coverage with the overcoats. A 1% solution of PEG-PLGA (1000 molecular weight PEG; 70 mol % lactic acid-30 mol % glycolic acid; inherent viscosity 0.45) in chloroform was sprayed over the DNA undercoat.

Figure 12:
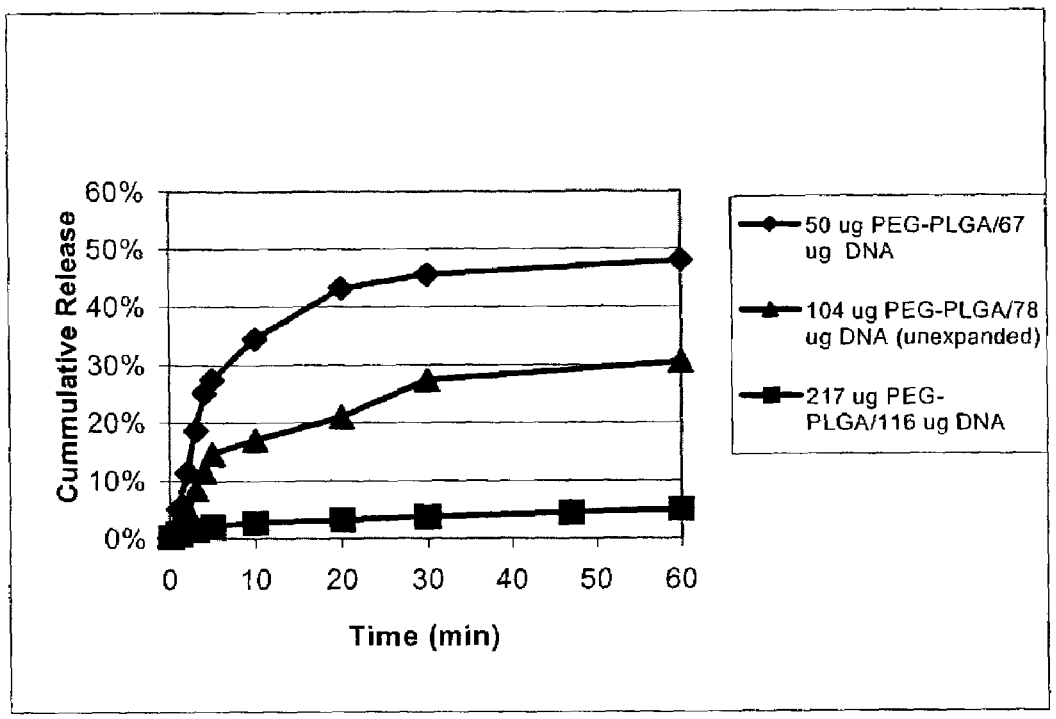
FIG. 12 is a graph of DNA release as a function of time for biodisintegrable coatings, according to an embodiment of the invention.

Upon examination under SEM, it was apparent that the stents with block copolymer overcoats of polyethylene glycol 1000/70:30 poly (DL-lactide-co-glycolide) (PEG-PLGA) became porous upon stent expansion. It is believed that the resulting porosity may enhance DNA diffusion, while also ensuring side branches of the vasculature do not become blocked. FIG. 12 graphically illustrates the release profile of DNA from PEG-PLGA coated stents at various DNA and polymer overcoat loadings. As can be seen from this figure, the PEG/PLA overcoats modulated DNA release. Increasing coating weights of PEG-PLGA were shown to decrease DNA release.

Figure 13:
FIG. 13 is a photograph of a stent after implantation in a rabbit iliac artery, according to an embodiment of the invention.

FIG. 13 is a photograph of a stent after seven days of implantation in a rabbit iliac artery. The stent was coated with plasmid DNA (containing a LacZ reporter gene) and subsequently provided with an overcoat of polyethylene glycol 1000/70:30 PEG-PLGA using procedures like those described above. β-galactosidase expression was used to assess transduction. Photographed from the adventitial surface, the dark staining observed around the stent struts in FIG. 13 is considered areas of cell transduction.

Figure 14:
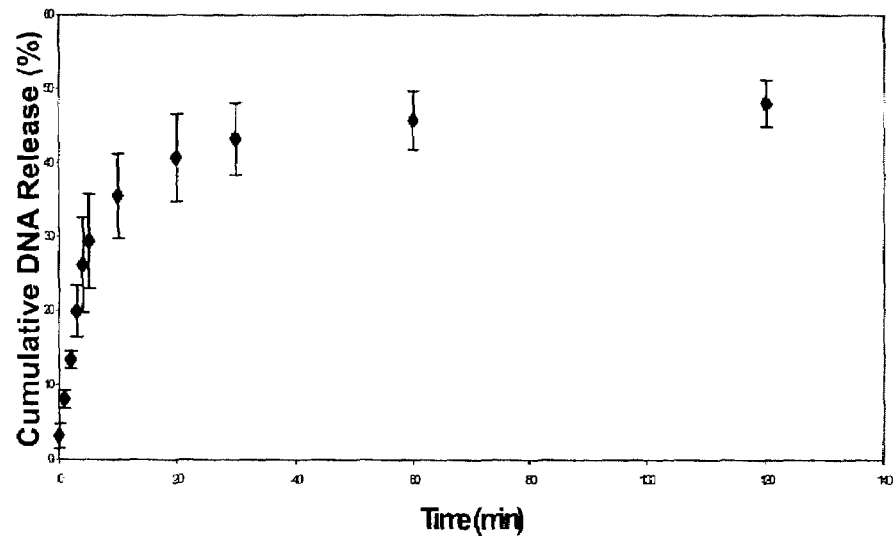
FIG. 14 is a graph of DNA release as a function of time for a biostable coating, according to an embodiment of the invention.

FIG. 14 graphically illustrates the release profile of DNA overcoated with a polystyrene-polyisobutylene-polystyrene triblock copolymer (SIBS) using procedures like those described above. The SIBS is produced using procedures like those described in U.S. Pat. No. 4,946,899 and United States Patent Application 20020107330. Incremental DNA release was observed over period of about 20 minutes. Although not illustrated, increasing coating weights of SIBS was shown to decrease DNA release.

Example 10

Figure 15:
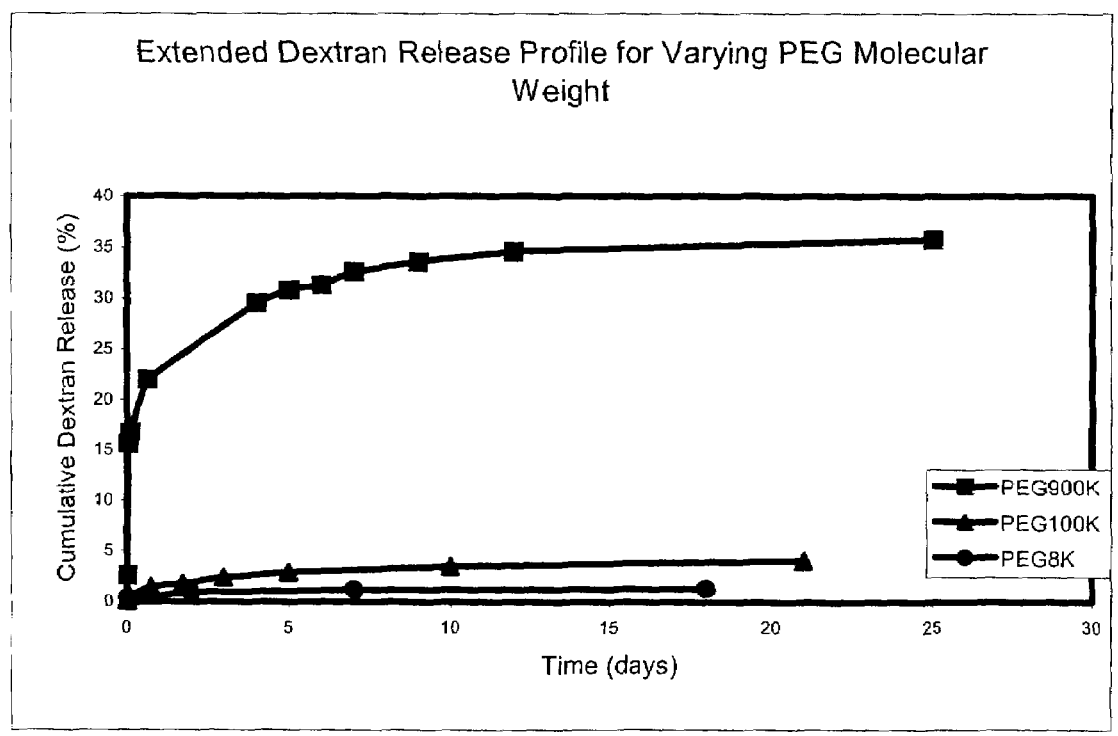
FIG. 15 is a graph of dextran release as a function of time for biostable coatings, according to an embodiment of the invention.

Addition of Polyethylene Glycol to Modulate Release of Dextran from a Polystyrene-Polyisobutylene-Polystyrene Triblock Copolymer Matrix To determine the effect of PEG molecular weight on FITC-dextran (fluorescein-isothiocyanate-dextran, MW 70,000, available from Sigma) elution from a SIBS coating, three formulations were studied, as seen in FIG. 15. Formulations included 4.9% SIBS with 0.1% PEG (either 900,000 MW, 100,000 MW, or 8,000 MW available from Polysciences) prepared with 10% FITC-dextran (based on the weight of the SIBS/PEG solids). The suspension was pipetted onto coupons and dried at room temperature for 3 hours. Coated coupons were immersed in PBS at 37° C. and release profiles were obtained using spectrofluorometric detection of the release of FITC-dextran. The amount of FITC-dextran released was derived from a calibration curve plotted with known concentrations of FITC-dextran.

FIG. 15 illustrates cumulative dextran release from a SIBS polymer matrix as a function of time for PEG of various molecular weights (i.e., 8,000, 100,000 and 900,000). As can be seen from this Figure, dextran release was substantially limited with the lower molecular weight PEGs (i.e., the 8,000 and 100,000 molecular weight PEGs), but not for the higher molecular weight PEG (i.e., the 900,000 molecular weight PEG).

Figure 16:
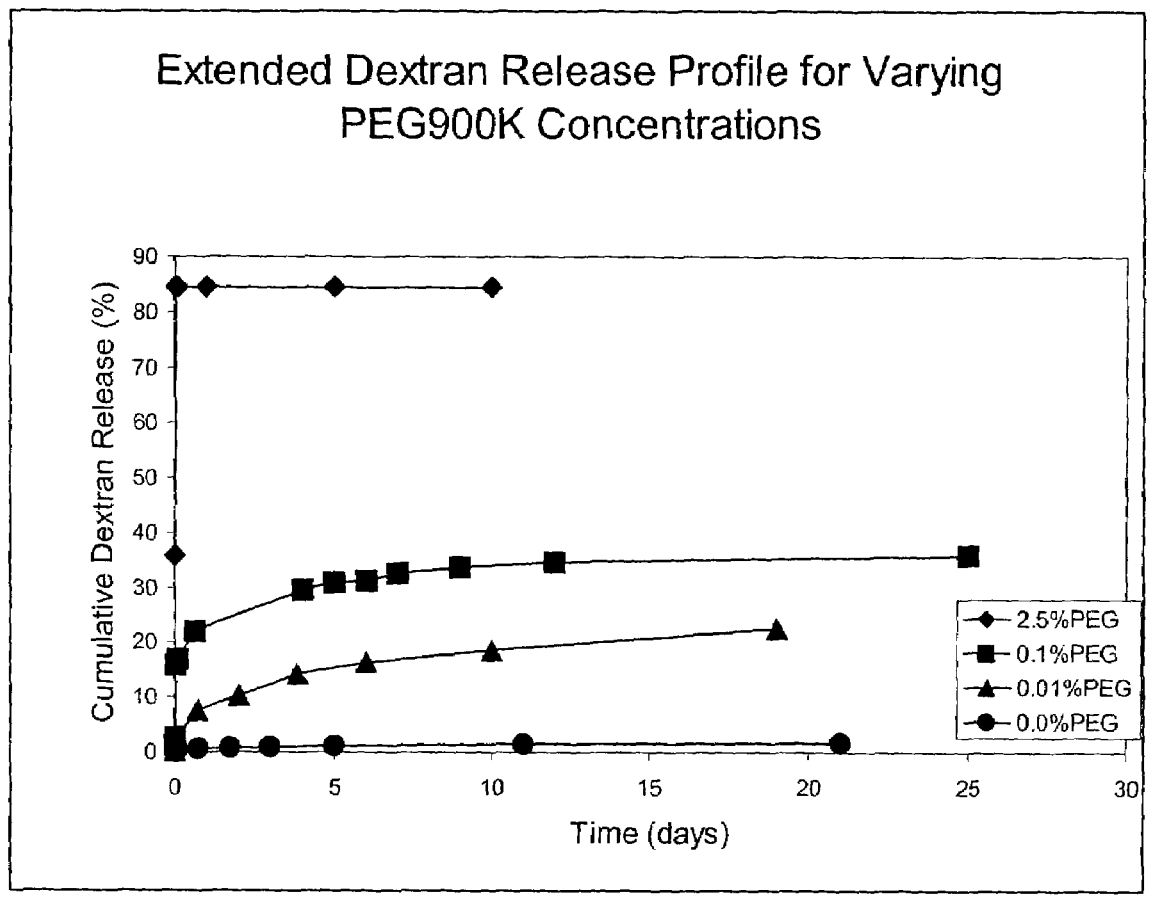
FIG. 16 is a graph of dextran release as a function of time for biostable coatings, according to an embodiment of the invention.

The methods associated with FIG. 15 were also used in connection with FIG. 16. In this case, FITC-dextran release was assessed as a function of the amount of PEG 900,000 MW used. The addition of SIBS was varied to achieve an overall solids content of 5%.

FIG. 16 illustrates cumulative dextran release as a function of time for various ratios of SIBS and PEG900K (i.e., 900,000 molecular weight PEG) within the SIBS polymer matrix. As can be seen from FIG. 16, The 2.5% SIBS/2.5% PEG900K formulations shows a large burst of release over a relatively short time period, whereas the 4.99% SIBS/0.01% PEG900K demonstrated much lower release over an extended time period.

Example 11

Addition of Micronized Sodium Chloride to Increase Porosity of a Polystyrene-Polyisobutylene-Polystyrene Triblock Copolymer Matrix A SIBS/NaCl suspension in chloroform was prepared (using 16% SIBS, 84% micronized NaCl) and immersed in a sonicator at maximum power for 5 minutes to facilitate dispersion. Coupons were dipped in the dispersion and dried at 70° C. under vacuum for 2 hours. The salt was then extracted from the coating by immersing the coupon in PBS for 22 hrs.

Figure 17:
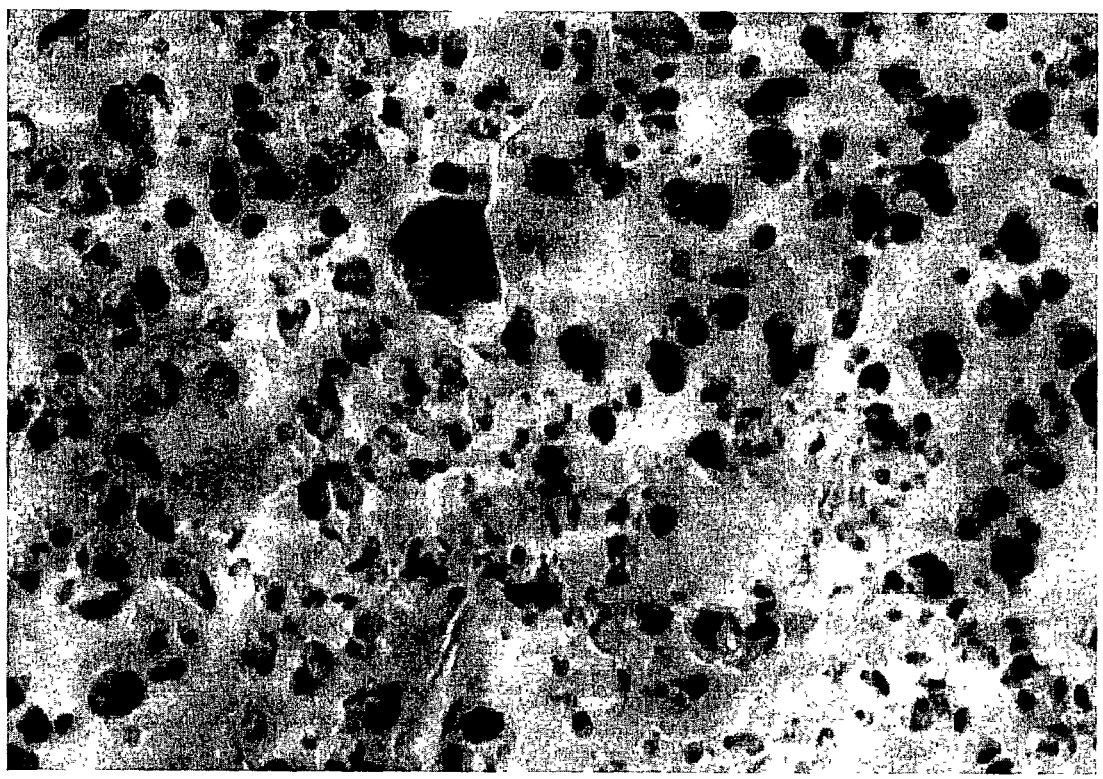
FIG. 17 is a photograph of a biostable coating material after NaCl extraction in PBS, according to an embodiment of the invention.

FIG. 17 is a micrograph of the 16% SIBS/84% micronized NaCl coating following 22 hours of extraction in PBS. The interconnected pores averaged 7 um in diameter.

Example 12

Addition of DNA and Poloxamer to a Polystyrene-Polyisobutylene-Polystyrene Triblock Copolymer Matrix 9000 ppm of poloxamer (P104) available from BASF was used to stabilize a water-in-oil emulsion. The coating formulation was prepared by mixing 9000 ppm P104 in toluene with SIBS. DNA (20 mg/ml stock solution) was added dropwise to a final organic:aqueous ratio of 3:1 (final formulation: 9000 ppm P104, 7.5% SIBS and 0.5% DNA). Stents were dipped into the emulsion and spun at 5000 rpm for 16 seconds. Samples were dried at 50° C. for 1 hour.

The use of 9000 ppm of poloxamer allowed a stable water-in-oil emulsion to be readily created with minimal mechanical mixing. In addition to assisting with emulsion formation, the use of the poloxamer further assisted in the formation of a porous polymer network. Moreover, as noted above, literature studies have demonstrated enhanced DNA transfection in the presence of poloxamers.

Figure 18:
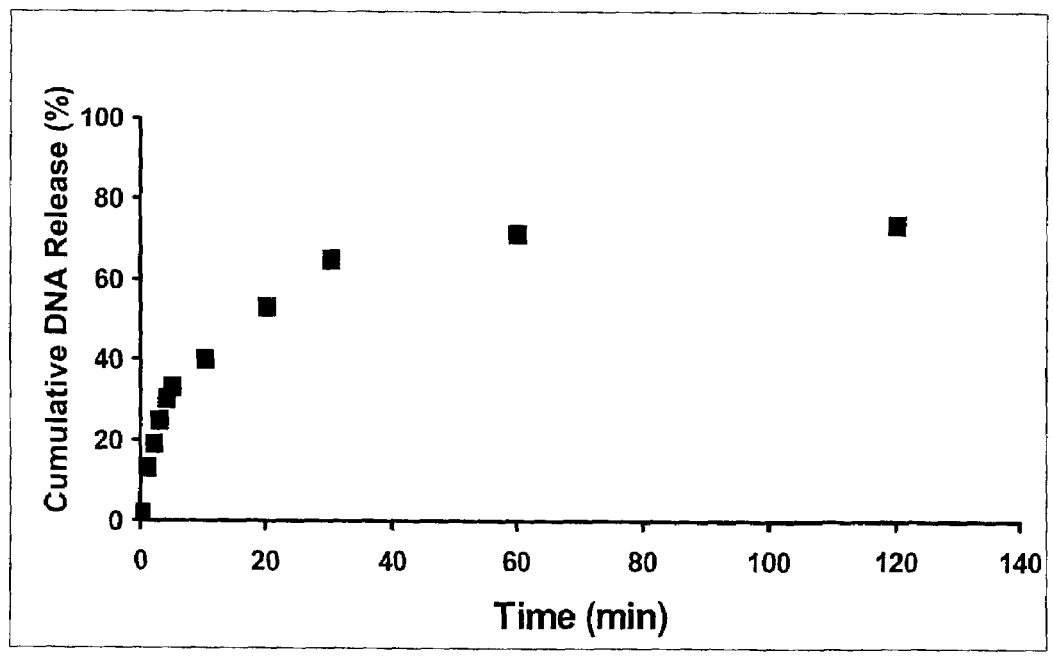
FIG. 18 is a graph of DNA release as a function of time for biostable coatings, according to an embodiment of the invention.

FIG. 18 is a graph of percent cumulative release as a function of time for a stent coated with a matrix of SIBS, DNA and poloxamer. As can be seen from this figure, 50% of the DNA release occurred between 0 and 20 minutes.

It will be apparent to those skilled in the art that various modifications and variations can be made in the structure and the methodology of the present invention, without departing from the spirit or scope of the invention, thus it is intended that the present invention covers the modifications and variations of this invention provided they come within the scope of the appended claims and their equivalents.

What is claimed is:

1. A medical device, at least a portion of which is insertable or implantable into the body of a patient, said medical device comprising: a therapeutic agent containing layer comprising a high-molecular-weight therapeutic agent; and a polymeric covering layer disposed over said therapeutic agent containing layer, said polymeric covering layer comprising one or more polymers selected from (a) a block copolymer comprising at least two polymeric blocks A and B, wherein A is a polyolefin block and wherein B is a vinyl aromatic block, (b) a polymer or copolymer of lactic acid, (c) a polymer or copolymer of glycolic acid, and (d) a tyrosine-based polymer or copolymer, said polymeric covering layer having regions of a leachable material dispersed within the polymeric covering layer.

2. The medical device of claim 1, wherein said polymeric covering layer comprises a block copolymer having at least two polymeric blocks A and B, wherein A is a polyolefin block of the general formula —(CRR'—CH.sub.2).sub.n-, where R and R' are linear or branched aliphatic groups or cyclic aliphatic groups and wherein B is a vinyl aromatic polymer block.

3. The medical device of claim 1, wherein said polyolefin block comprises one or more monomers selected from ethylene, butylene and isobutylene and wherein said vinyl aromatic polymer block comprises one or more monomers selected from styrene and .alpha.-methylstyrene.

4. The medical device of claim 1, wherein said polymeric covering layer comprises a copolymer of lactic acid and glycolic acid.

5. The medical device of claim 1, wherein said polymeric covering layer comprises a tyrosine-derived polycarbonate.

6. The medical device of claim 1, wherein said therapeutic agent containing layer is applied by dipping at least a portion of said medical device into a solution comprising said high-molecular-weight therapeutic agent.

7. The medical device of claim 1, wherein the medical device is selected from a catheter, a balloon, a filter, a coil, a clip and a sling.

8. The medical device of claim 1, wherein the medical device is an intraluminal stent.

9. The medical device of claim 8, wherein said intraluminal stent is a vascular stent.

10. The medical device of claim 1, wherein said high-molecular-weight therapeutic agent is selected from (a) polysaccharide therapeutic agents having a molecular weight greater than 1,000; (b) polypeptide therapeutic agents having a molecular weight greater than 10,000; and (c) polynucleotides having a molecular weight greater tan 2,000.

11. A medical device, at least a portion of which is insertable or implantable into the body of a patient, said medical device comprising: a polymeric layer comprising (a) a block copolymer comprising at least two polymeric blocks A and B and a removable component, wherein A is a polyolefin block and wherein B is a vinyl aromatic block or (b) a tyrosine-based polymer or copolymer and a removable component comprising a leachable material ; and a high-molecular-weight therapeutic agent disposed below or within said polymeric layer, said polymeric covering layer having regions of the leachable material dispersed within the polymeric covering layer.

12. The medical device of claim 11, wherein said polymeric layer comprises a block copolymer having at least two polymeric blocks A and B, wherein A is a polyolefin block of the general formula —(CRR'—CH.sub.2).sub.n-, where R and R' are linear or branched aliphatic groups or cyclic aliphatic groups and wherein B is a vinyl aromatic polymer block.

13. The medical device of claim 11, wherein said polyolefin block comprises one or more monomers selected from ethylene, butylene and isobutylene and wherein said vinyl aromatic polymer block comprises one or more monomers selected from styrene and .alpha.-methylstyrene.

14. The medical device of claim 11, wherein said polymeric layer comprises a tyrosine-derived polycarbonate.

15. The medical device of claim 11, wherein said medical device is selected from a catheter, a balloon, a filter, a coil, a clip and a sling.

16. The medical device of claim 11, wherein said medical device is an intraluminal stent.

17. The medical device of claim 16, wherein said intraluminal stent is a vascular stent.

18. The medical device of claim 11, wherein said polynucleotide is plasmid DNA.

19. The medical device of claim 11, wherein the removable component is a leachable material.

20. The medical device of claim 19, wherein the leachable material is selected from one or more of the following: polyethylene glycols, polyalkylene oxides, polyhydroxyethylmethacrylates, polyvinylpyrrolidones, polyacrylamide and its copolymers, liposomes, proteins, peptides, salts, sugars, polysaccharides, polylactides, cationic lipids, detergents, polygalactides, polyanhydrides, polyorthoesters and their copolymers, and soluble cellulosics.

21. The medical device of claim 20, wherein the leachable material is a salt.

22. The medical device of claim 20, wherein the leachable material is a polyalkylene oxide selected from (a) polyethylene oxide and (b) copolymers of polyethylene oxide and polypropylene oxide.

23. The medical device of claim 11, wherein said high-molecular-weight therapeutic agent is disposed below said polymeric layer.

24. The medical device of claim 11, wherein said high-molecular-weight therapeutic agent is disposed within said polymeric layer.

25. The medical device of claim 11, wherein said high-molecular-weight therapeutic agent is selected from polysaccharide therapeutic agents having a molecular weight greater than 1,000; polypeptide therapeutic agents having a molecular weight greater than 10,000; and polynucleotides having a molecular weight greater than 2,000.

* * * * *

UNITED STATES PATENT AND TRADEMARK OFFICE
CERTIFICATE OF CORRECTION

PATENT NO. : 7,491,234 B2
APPLICATION NO. : 10/308587
DATED : February 17, 2009
INVENTOR(S) : Maria Palasis et al.

It is certified that error appears in the above-identified patent and that said Letters Patent is hereby corrected as shown below:

Specification, Col. 3, line 3, after "can be", delete "is".

Claim 10, Col. 28, line 19, after "greater", change "tan" to -- than --.

Signed and Sealed this

Twenty-first Day of April, 2009

JOHN DOLL
*Acting Director of the United States Patent and Trademark Office*